United States Patent
Gimenez et al.

(10) Patent No.: US 8,815,506 B2
(45) Date of Patent: Aug. 26, 2014

(54) METHOD FOR THE IN VITRO DIAGNOSIS OR PROGNOSIS OF TESTICULAR CANCER

(75) Inventors: Juliette Gimenez, Caluire et Cuire (FR); Cecile Montgiraud, Lyons (FR); Francois Mallet, Villeurbanne (FR)

(73) Assignee: Biomerieux, Marcy l'Etoile (FR)

( * ) Notice: Subject to any disclaimer, the term of this patent is extended or adjusted under 35 U.S.C. 154(b) by 610 days.

(21) Appl. No.: 12/918,126

(22) PCT Filed: Mar. 10, 2009

(86) PCT No.: PCT/FR2009/050388
§ 371 (c)(1),
(2), (4) Date: Aug. 18, 2010

(87) PCT Pub. No.: WO2009/122052
PCT Pub. Date: Oct. 8, 2009

(65) Prior Publication Data
US 2010/0330580 A1    Dec. 30, 2010

(30) Foreign Application Priority Data

Mar. 12, 2008   (FR) ..................................... 08 51621

(51) Int. Cl.
*C12Q 1/68*   (2006.01)
*C12P 19/34*  (2006.01)
*C12Q 1/70*   (2006.01)

(52) U.S. Cl.
CPC .............. *C12Q 1/686* (2013.01); *C12Q 7/6886* (2013.01); *C12Q 1/702* (2013.01); *C12Q 2535/125* (2013.01); *C12Q 2600/154* (2013.01)
USPC .......................................... 435/6.1; 435/91.2

(58) Field of Classification Search
CPC .. C12Q 1/702; C12Q 2535/125; C12Q 1/686; C12Q 1/6886; C12Q 2600/154
See application file for complete search history.

(56) References Cited

U.S. PATENT DOCUMENTS 5,858,723 A    1/1999   Mueller-Lantzsch et al.

OTHER PUBLICATIONS

Gimenez and Mallet; Atlas of Genetic and Cytogenetics in Oncology and Haematology, 2008, vol. 12, pp. 134-148, published Sep. 2007.*
Pichon et al; Nucleic Acids Research, vol. 34, 2006, e46, pp. 1-10.*
Matouskova et al; Experimental Cell Research, vol. 312, 2006, pp. 1011-1020.*
Lavie et al; Journal of Virology, vol. 79, 2005, pp. 876-883.*
Yi et al., "Expression of the human endogenous retrovirus HERV-W family in various human tissues and cancer cells," *Journal of General Virology*, vol. 85, No. Pt. 5, pp. 1203-1210, May 1, 2004.
Matouskova et al., "CpG methylation suppresses transcriptional activity of human *syncytin-1* in non-placental tissues," *Experimental Cell Research*, vol. 312, No. 7, pp. 1011-1020, Apr. 15, 2006.
Lavie et al., "CpG Methylation Directly Regulates Transcriptional Activity of the Human Endogenous Retrovirus Family HERV-K(HML-2)," *Journal of Virology*, vol. 79, No. 2, pp. 876-883, Jan. 2, 2005.
Nickerson et al., "DNA sequence diversity in a 9.7-kb region of the human lipoprotein lipase gene," *Nature Genetics*, vol. 19, pp. 233-240, Jul. 1998.
Cottrell, Susan E., "Molecular diagnostic applications of DNA methylation technology," *Clinical Biochemistry*, vol. 37, pp. 595-604, 2004.
Written Opinion of the International Searching Authority issued in Application No. PCT/FR2009/050388; Dated Sep. 15, 2009 (With Translation).
International Search Report issued in Application No. PCT/FR2009/050388; Dated Sep. 15, 2009 (With Translation).

* cited by examiner

*Primary Examiner* — Jehanne Sitton
(74) *Attorney, Agent, or Firm* — Oliff PLC

(57) ABSTRACT

A method for in vitro diagnosis or prognosis of testicular cancer in a biological sample from a patient suspected of suffering from testicular cancer, having a step of detecting the presence or absence of methylation of CpG dinucleotides in at least one genomic DNA target sequence of the sample, the target sequence being selected from at least one of the sequences identified in SEQ ID NOS: 1 to 7 or from at least one sequence which exhibits at least 99% identity with one of the sequences identified in SEQ ID NOS: 1 to 7 and the sequences complementary thereto; to the DNA sequences and to the use thereof as a testicular cancer marker.

14 Claims, 9 Drawing Sheets

HW2TT Locus

Normal testicle 12 clones

Tumoral testicle 12 clones

HW21TT Locus

SEQUENCE LISTING

```
<160> NUMBER OF SEQ ID NOS: 49

<210> SEQ ID NO 1
<211> LENGTH: 255
<212> TYPE: DNA
<213> ORGANISM: Homo sapiens

<400> SEQUENCE: 1
tgagaaacag gactagttag atttcctagg ccaactaaga atccctaagc ctagctggga      60
aggtgatcgc atccaccttt aaacacgggc ttgcaactta gctcacacct gaccaatcag     120
gtagtaaaga gagctcacta aaatgctaat taggcaaaaa caggaggtaa agaaatagcc     180
aatcatctat tgcctgacac cacacgggga gggacaatga ttgggatata aacccaggaa     240
ttcgagctgg caacg                                                      255

<210> SEQ ID NO 2
<211> LENGTH: 247
<212> TYPE: DNA
<213> ORGANISM: Homo sapiens

<400> SEQUENCE: 2
tgagacacag gactagctgg atttcctagg ccgactaaga atccctaagc ctagctggga      60
aggtgaccac atccaccttt aaacacgggg tttacaactt agctcacacc cagccaatca     120
gagagctcac taaaatgcta attaggcaaa aacaggaggt aaagaaatag ccaatcatct     180
attgcctgag agcacagcgg gagggacaag gattgggata taaacccagg cattcgagct     240
ggcaacg                                                               247

<210> SEQ ID NO 3
<211> LENGTH: 241
<212> TYPE: DNA
```

<213> ORGANISM: Homo sapiens

<400> SEQUENCE: 3

| | |
|---|---|
| tgagagacag ctggatttcc taggccgact aagaatccct aagcctagct gggaaggtga | 60 |
| ccgcatccac ctttaaacac agggcttgca acttagctca cacccaacca atcagagagc | 120 |
| tcactaaaat gctaattagg caaaaacagg aggtaaagaa atagcaagtc atctattgcc | 180 |
| tgagagcaca gtgggaggga caaggaccag gatataaacc caggcatttg agccagcaac | 240 |
| g | 241 |

<210> SEQ ID NO 4
<211> LENGTH: 248
<212> TYPE: DNA
<213> ORGANISM: Homo sapiens

<400> SEQUENCE: 4

| | |
|---|---|
| tgagagacag gactaactgg atttcctagg ccgactaaga atccctaagc ctagctggga | 60 |
| aggtgaccgc atccatcttt aaacacgggg cttgaaactt agctcacacc taaccagtca | 120 |
| gagagctcac taaatgcta attaggcaaa aacaggagg taaagaaata gccaatcatc | 180 |
| tattgcctga gagcacagcg ggagggacaa ggatcgggat ataaacccag gcattcgagc | 240 |
| cagcaatg | 248 |

<210> SEQ ID NO 5
<211> LENGTH: 255
<212> TYPE: DNA
<213> ORGANISM: Homo sapiens

<400> SEQUENCE: 5

| | |
|---|---|
| tgagagacag gactagctgg atttcctagg ccgactaaga atccctaagc ctagctggga | 60 |
| aggtgaccgc ttccaccttt aaacacgggg cttgcaactt agctcacacc cgaccaatca | 120 |
| gatagtaaag agagcacact aaaatgctaa ttaggcaaaa acaggaggta aagaaatagc | 180 |
| caatcatcta ttgcctgaga gcaaagcggg agggacaatg atcgggatag aaacccaggc | 240 |
| attcaagccg gaatg | 255 |

<210> SEQ ID NO 6
<211> LENGTH: 247
<212> TYPE: DNA
<213> ORGANISM: Homo sapiens

<400> SEQUENCE: 6

| | |
|---|---|
| tgagagacag gactagctgg atttcctagg ccgactaaga atccctaagc ctagctggga | 60 |
| aggtgaccac gtccaccttt aaacacgggg cttgcaactt agctcacacc tgaccaatca | 120 |
| gagagctcac taaatgcta attaggcaaa gacaggaggt aaagaaatag ccaatcatct | 180 |
| attgcctgag agcacagcag gagggacaac aatcgggata taaacccagg cattcgagct | 240 |
| ggcaaca | 247 |

<210> SEQ ID NO 7
<211> LENGTH: 314
<212> TYPE: DNA
<213> ORGANISM: Homo sapiens

<400> SEQUENCE: 7

| | |
|---|---|
| ccctggggcg ggcttccttt ctgggatgag ggcaaaacgc ctggagatac agcaattatc | 60 |
| ttgcaactga gagacaggac tagctggatt tcctaggccg actaagaatc cctaagccta | 120 |

```
gctgggaagg tgaccacgtc cacctttaaa cacggggctt gcaacttagc tcacacctga      180
ccaatcagag agctcactaa aatgctaatt aggcaaagac aggaggtaaa gaaatagcca      240
atcatctatt gcctgagagc acagcaggag ggacaacaat cgggatataa acccaggcat      300
tcgagctggc aaca                                                        314
```

<210> SEQ ID NO 8
<211> LENGTH: 7774
<212> TYPE: DNA
<213> ORGANISM: Homo sapiens

<400> SEQUENCE: 8

```
tgagacacag gactagctgg atttcctagg ccgactaaga atccctaagc ctagctggga       60
aggtgaccac atcccctttt aaacacgggg tttacaactt agctcacacc cagccaatca      120
gagagctcac taaaatgcta attaggcaaa acaggaggt aaagaaatag ccaatcatct       180
attgcctgag agcacagcgg gagggacaag gattgggata taaacccagg cattcgagct      240
ggcaacggca accccctttg ggtctcctcc ctttgcatag gagctctgtt ttcactctat      300
taagtcttgc aactgcactc ttctggtccg tgtttcttac cgcttgagct gagcttttcc      360
tcactgtcca ccactgctgt tttgccaccg tcacaggccc accgctgact tccattcttc      420
tggatctagc aggctgtcca ctgtgctcct gatccagcga ggcgcccatt gccgctcccg      480
attgggctaa aggcttgcca ttgttcctgc atggctacgt gcctgggttc atcctaatca      540
agccgaacac tagtcactgg gttccacggt tctcttccat gacccacgac ttctaataga      600
actataacac tcacctcatg gcccaagatt ccattccttg gaatccatga ggccaagaac      660
cccaggtcag agaacacgag gcttgccacc atcttggaag tggccccacc accatcttgg      720
gagctctggg agcaaggacc cccggtaaca ttttggcgac cacaaaggga catccaaagt      780
ggtgagtaat attggaccac tttcacttgc tattctgttc tatccttcct tagaactgga      840
ggaaaatacc aggcacaggc acctgtcagc cagttaaaaa caattagcgt cgccgccaca      900
cttaagactc aggtgtgagg ctatctgggg aaagactttc taacaacccc caacccatct      960
agtggggatg ttggtctgcc tggagacagc ttccactttc aattttcttg gggaagccga     1020
gggctcacta gaggcagaca gctgttgtcc caaactccgg gcagtagccg gttgagatca     1080
tggtgcagcc aggagtctct actcagcagt cgccgatgca tgtgcccta ccttcccttc      1140 tgacccatac atcctgagtc ccgactgtga cttcttgaa agtgtagccc caaaattctc      1200
cttacctctg aatctacttc ctctgatccc tgcctcctgg gtactaatga ttcagacttt     1260
catttcctct agcaagttgt gtctccaaag ggatctaagg aggctctacg ctgcatcctt     1320
aggcacctag gctataaccc aaggagtctt atccctggtg tccctcccga tttgggtata     1380
caactctcaa catgggcagt tatgtaggac ccattcccca ccacacttgc cagggcccca     1440
agtttgtaat ggctaagaga gagacacaga gagagagaga gagatggaga gagagacaag     1500
gagggagtca agagaaaaa gaaagaaaaa gaaatagtag aaaaaaaagt gtgccctatt      1560
cctttaaaag ccagggtaaa tttaaaacct gtaattgata attgaaggtc ttctccgtga     1620
ccctgtaaca ctccaatgcc atttgttgt cagtgtaaat aagggcatag cccaaaagca     1680
ctgaggtcac tgacaacccg tagctttccc atcaaaaatc cttacccag taatccgcgg      1740 atgggccaaa tgcattcagt cggtagcagc aaccgcttt g ctaaaagtag aaaagtaact     1800
tttagaggaa acctcattgt gagcgcacac ctcaccagtt cagaattatt ctaagtcaaa     1860
```

```
aaaaaaaaaa gcaaaaaggt aacttactaa ctcaaaaatc ttaaagtata ggtctatcat    1920
attagaaaag ggtaatgtaa ctccaaccac tgataattcc cttaacccag cagatttcct    1980 aacagggggat ttaaaactta attaccatac aaaggtccca ccagacctag gaggaactcc   2040
cttcaggaca ggacgataaa cggttcctcc caggtgattg aggaaaaaaa ccacaatggg    2100
tattcagtaa ttgatacaga gactcatgtg gaagcagtta gaaaaattgc ctaataattg    2160
gtctcctcaa acgtgtaagc tgtttgcact cagccaagcc ttaaagtact tacagaatca    2220
aaaagactct gaatcctgac tcaaaaggtt tgctacaccc tctgtgaaac aaatttgcat    2280
aagaactgtt gtttatggga aggcatcttg atggggcagc tgggttgtta tgaaatactc    2340 aggacccccag cccggctcta ggactcaccc ctgagcgcaa aaggcaatgt tgggcacgct   2400
ggtaaaggac cactagaatc cagcagcccg gaccccttc tttgtggtca agagaggcgg    2460
gaaaacaggt gcaggactgc tacatcagtg agcataacta atccagtaag cagaggtcca    2520
tgggtggtta tgcaccctgg aaagaatac gcattaggcc cttagaggat gctctaggac    2580
taatgctcat cggaaaatga ctaggggtgc tgacatccct atgttctttt ttcagatggg    2640
aaacgttcct cccaccccaa ggcaaaaaac acccctaaga tgtatttttgg agaattagga   2700 ccaatttgac cctcagacac taagaaagaa atgacttaca ttcttctgca gtaccatgat    2760
atcctcttca agggggagaa acctggcctc ctgagagaag tataaattat aacaccatct    2820
tacagtgaga cctcttctgt agaaaggagg gcaaatggag tgaagtgcaa actttccttt    2880
cattaagaga caactcgcaa ttatgtaaaa agtgtgattt atgccctaca gaaagccctc    2940
agtctacctc cctatcccag ggtcccccg attccttttcc caactaataa ggaccccct    3000 tttacccaaa tggtccaaag gagatagatg aagggataaa caatgaacca aacagtgcca    3060
atattccctg attatgcccc ctccaggcag tgggaggagg agaattcggc ccagccagag    3120
tgcatgtacc ttttttttttc tctcagactt aaagcaaatt aaaatagacc taggtaaatt    3180
ctcagataac cctgatggct atattgatgt tttacaaggg ttaggacaat cctttgctct    3240
gacatggaga gatataatgt tactgctaaa tcagacacta accccaaatg agagaagtgt    3300
caccatagct gcagcccaag agtttggcaa tctctggtat ctcagtcagg tcaatgatag    3360
gatgacaaca gaggaaaggg aatgattccc cacaggccag caggcagttc tcagtgtaga    3420
ccctcactgg gacacagaat aagaacatgg agatcggtgc cgcagatatt tgctaacttg    3480
cgtgctagga ctaaggaaaa ctaggaagaa gcctatgaat tattcagtga tgtccactat    3540
aacacaggga aaggaagaaa atcatactgc cttccggaa atactaaggg aggcattgag    3600
gaagcatacc tctctgtcac ctgactgtat tgaagtccaa ctaatcttaa aggatatgtt    3660
tatcactcag tcagctgcag acattagaaa aaacttcaaa agtccacctt aggcccagag    3720
caaaacttag aaaccctatt gaacttgtta acctcagttt tttataatag agatcaggag    3780
gagcaggcgg aacaggacaa acaggattaa aaaaagacca ccgctttagt catggccctc    3840
aggcaagtgg actttggaag ctctggaaaa gggaaaagct gggcaaattg aatgcctaat    3900
agggcttgct tccagtgtgg tctacaagga cacttaaaaa aagattgtcc aagtagaaat    3960
aagctgcccc ttcgtccatg cctcttatgt caagggaatc actggaaggc ccattgcccc    4020 agggggaggaa ggtcctctga gtcagaagcc actaaccaga tgatccagca gcaggactaa    4080
gggtgcccag ggcaagcccc agcccatgcc atcaccctca cagagcccg ggtatgcttg     4140 accattgagg gccaggaggt taactgtctc ctgaacactg gcacagcctt tcagtcttca    4200 cttttcctgtc ccggacaact gtcctccaga tctgtcacta tctgagcggt cctaggacag    4260
```

```
ccagtcacta gatatttctc ccagccacta agttgtgact ggggaacttt actcttttca    4320 catgctttc  taattatgcc tgaaagcccc actcctttgt tagggagaga cattctagca    4380
aaagcagggg ccattataca tctgaacata ggagaaggaa cacccgtttg ttgtcacctg    4440
cttgaggaag gaattaatgc tgaagtctgg gcaacagaag gacaatatgg atgagcaaag    4500
aatgcccatc ctgttcaagt taaattaaag gattccgcct cctttcccta ccaaaggcaa    4560 tacccccttta gacccgaggc ccaacaagga ctccaaaaga ttgttaagga cctaaaagcc    4620
caaggcctag taaaaccatg caatagcccc tgccatactc caattttagg agtaaggaaa    4680
cccaacggac agtggaggtt agtgcaagaa ctcaggatta tcaatgaggc tgttgttcct    4740
ctatacccag ctgtacctaa cccttataca gtgctttccc aaataccaga ggaagcagag    4800
tggtttacag tcctggacct taaggatgcc ttttctgca  tccctgtacg tcctgactct    4860
caattcttgt ttgcctttga agatcctttg aacccaacgt ctcaactcac ctggactgtt    4920
ttaccccaag ggttcaagga tagccccat  ctatttggcc aggcattagc ccaagacttg    4980
agccaattct catacctgga cactcttatc cttcggtatg gggatgattt aattttagct    5040
acccattcag aaacgttgtg ccatcaagcc acccaagtgc tcttaaattt cctcgctacc    5100
tgtggctaca ggtttccaaa cgaaaggctc agctctgctc acagcaggtt aaatacttag    5160
ggctaaaatt atccaaaggc accagggccc tcagtgagga acgtatccag cctatactgg    5220
cttattctca tcccaaaacc ctaaagcaac taagagcatt ccttggcata acaggctgct    5280
gctgaatatg gattcccagg tacagtgaaa tagccaggcc attatacaca ctaattaagg    5340
aaactcagaa agccaatacc catttagtaa gatggacacc ttaagcagaa gcggctttcc    5400
aggccttaaa gaaggcccta acccaagccc cagtggtaag cttgccaaca gggcaagact    5460 tttcttata  tgtcacagaa gaaacaggaa tagctctagg agtccttaca caggtctgag    5520
ggatgagctt gcaacccatg gcatacctga gtaaggaaac tgatgtagtg caaagggtt    5580 ggcctcattg tttacgggta gtggcagcag tagcagtctt agtatctgaa gtagttaaaa    5640
taatacaggg aagagatctt actgtgtgaa catctcatga tgtgaatggc atagtcactg    5700
ctaaaggaga cttgtggctg tcagacaact gtttacttaa ataccaggct ctattacttg    5760
aagggccagt gctgcgactg tgcacttgtg caactcttaa cccagacaca tttcttccag    5820
acaatgaaga aaagatagaa cataactgcc aacaagtaat tgctcaaacc tatgccactc    5880
gaggggacct tttagaggtt cccttgactg atcccaacct caacttgtat actgatggaa    5940
gttcctctgt agaaaaagga ctttgaaaag tggggtatgc agtggtcagt gataatggaa    6000
tacttgaaag taatcccctc actccaggaa ctagtgctca gctggcagaa ctaatagccc    6060
tcactcgggc actagaatta ggagaagaga aaagggtaaa tatatacaga ctctaagtat    6120
gcttacctag tcctccatgc ccatgcagca atatggagag aaagggaatt cctaatttcc    6180
aagggaacac ctatccaaca tcaggaagcc attaggagat tactattggc tgtacagaaa    6240
cataaagagg tggcaatctt acactgccgg tgtcaccaga aaggaaagga aagggaaata    6300
gaaaggaacc accaagcgga tattgaagcc aaaagagccg caaggcagga ccctccatta    6360
gaaatgctta tagaaggacc cctagtatgg ggtaatcccc tccaggaaac caagcccag    6420 tactcagaag aagaaataga atgaggaacc tcacaagcac atagtttcct cccctcagga    6480
tggctagcca ctgaagaagg aaaaatactt ttgcctgcag ctaaccaatg gaaattactt    6540
aaaacccttc accaaacatt tcccttaggc attgatagca cccatcagat ggccaaatta    6600
```

| | |
|---|---:|
| ttatttactg gaccaggcct tttcaaaact atcaagcaga tagtcagggc ctgtaaagtg | 6660 |
| tgccaaacaa gtaatccct gcactgcagg ccatacattt caatccctgt atctttaacc | 6720 |
| tccttgttaa gtttgtctct tccagaatca aagctgtaaa actacaaata gttcttcaaa | 6780 |
| tggagcccca gatgtagtcc atgactaaga tctaccgcgg acccctggac aagcctgcta | 6840 |
| gcccatgctc tgatgttaat gacatggaag gcacccctcc cgaggaaatc gcaactgcac | 6900 |
| aaccccctatt acaccccaat tcagcaggaa gcagttagag cattcatcag ccaacctccc | 6960 |
| caacagcact tgggttttcc tattgagagg gggtactgag agacaggact agctggatgt | 7020 |
| cctaggctga ctaagaatcc ctaagcctag ctgggaaggt gaccacatcc accttaaat | 7080 |
| acggggcttg caacctagct cacacccaac agatcagaga gctcgttaaa atgctaatta | 7140 |
| ggcaaaaaca ggaggtaaag aaatagccaa tcatctattg cctgagagca cagcaggagg | 7200 |
| gacaaggatt gggatataat cccaggcatt cgagctggca acagcaaccc cctttgggtc | 7260 |
| ccctccctt gtatgggagc tgttttcact ctatttcact ctattaaatc ttgcaactgc | 7320 |
| actcttctgg tgcatgtttg ttactgcttg agctgaactt tcactcgcca tctaccactg | 7380 |
| ctgttttgcc gccgtcgcag acccactgct gacttccatt cttctggatc cagcagggtg | 7440 |
| tccactgtgc tcctgatcca gtgaggcacc cattgccgct cccgatctgg ctaaaggctt | 7500 |
| gccattgttc ctgcatcgct aagtgcctgg gttcgtccta atcaagctga acactagtca | 7560 |
| ctgggttcca cagttctctt ccatgaccca cgacttctaa tagagctata acactcacct | 7620 |
| tatgcccaa gattccattc cttggaatcc atgaggccaa aaaccccagg tcagagaaca | 7680 |
| tgagacttgc caccatgttg aagtggcctg ctgccatttt ggaagtggcc caccaccatc | 7740 |
| ttgggagctc tgggagcaag gacccctggt aaca | 7774 |

<210> SEQ ID NO 9
<211> LENGTH: 7487
<212> TYPE: DNA
<213> ORGANISM: Homo sapiens
<400> SEQUENCE: 9

| | |
|---|---:|
| tgagaaacag gactagttag atttcctagg ccaactaaga atccctaagc ctagctggga | 60 |
| aggtgatcgc atccaccttt aaacacgggc ttgcaactta gctcacacct gaccaatcag | 120 |
| gtagtaaaga gagctcacta aaatgctaat taggcaaaaa caggaggtaa agaaatagcc | 180 |
| aatcatctat tgcctgacac cacacgggga gggacaatga ttgggatata aacccaggaa | 240 |
| ttcgagctgg caacggcaac tccctttggg tctcctctca ttgtatggga gctctgtttt | 300 |
| cactctatta aatcttgcaa ctgcacactc ttctggtctg tgtttgttat ggcttgagct | 360 |
| gagcttttgc tggctgtcca ccactgctgt ttgctgccgt cgcagacccc ttgctgactc | 420 |
| ccacccctgc ggatctggca gggtgtctgc tgcgctcctg atccagccag gcacccactg | 480 |
| ctgctcccaa tcaggctaaa ggcttgccat tgttcctgca tggctaagtg cccgggttcg | 540 |
| tgctaattga gctgaacact agtcgctggg ttccacagtt ctcttccgtg acccacagct | 600 |
| tctaatagag ctataacact cactgcatgg cccaacattc cattccttgg aatctgtgag | 660 |
| gccaagaacc cccggtcaga gaacaagaag cttgccacca tcttggaagc agcccgccac | 720 |
| cattttggga gctctaagaa caaggacccc ccagtaacat tttggtgacc acgaagggac | 780 |
| ctccaaagca gtgagtaata ttgaaccact tccgcttgct attctgtcct aaccttcctt | 840 |
| agaattggag gaaaataccg ggcacctgtc ggccagttaa gaacgattag cgtgccgcc | 900 |
| agacttaaga ctctggtgtg aggctgtctg ggaaagggct ttctaacaac ccccaaccct | 960 |

```
tccgggttgg gagctttggt ctgcctggaa ccagcttcca ctttcaattt tcctggggaa    1020
tccaagggct gactagaggc agaaagctgt catcccgaac tcctggcatt agacagttga    1080
gatcgtggcg cagccagaag tctctactca acagtcaccc atgcgtgcac ccctaccttt    1140
ccttctaacc catacctccc gggtcccaac catgactttc ttgaaagtgt agcccctaaa    1200
ttctctttac ctctaaatct acttcttctc atccctgctt cctaggtact aatggttcag    1260
actttcattt cctctagcaa gttctatctc cagagggatc taaggaaggg atctatgctg    1320
tgtccttagg cccctaggct atgaacccag agagtcttct ccctgttatc tctccccatt    1380
taggcataca gctctcaaca tggacagtta tgtgggaccc attccctacc acccttgcca    1440 gggcccaag ttttcaaagg ctagaagaa aaaagagaga agagagaga gaggcagagg    1500 ggagagaaag agagagagac aaagagggag tcaaagagag atagaaagag aaagatagaa    1560
ctagtaaaga aaaaagtat gccccattcc tttaaaagcc agggtaaatt taaaacctat    1620
aattgataat tgaaggtctt ctccatgacc ctataacact ccaataccac cttgttttca    1680
gtgtaaacaa gggtgtagcc cgaaaacact gagaccactg acaacccata gccttcctat    1740
caaaaatcct taacccagga acccatggat ggcccaaatg cattcaatct gtagcagcaa    1800
ctgctttgct aacagaagaa agtagaaaag taacttttag agaaaacctc attgtgagca    1860
cacctcacca gttcagaatt attctaagtc aaaaaagcaa aaaggtagct tactaactca    1920
aaaatcttaa agtatggggt tattctgtta gaaaaaggtg atttaacatt aaccactgaa    1980
aattccctta acccagcagg tttcctaatg ggatttaaat cttcattacc atacaaaggt    2040
ccgaccagac ccagcaggaa ctccctttag gacaggatga tagatggttc ctcctgggtg    2100 attgagggggg tgaaaaacca caatgggtgt tcagtaattg ataggagac tcttgtggaa    2160 ggagagttag gaaaattgcc taataattgg tctgctcaaa tgtgcgagct gtttgcactc    2220
agccaagcct taaagtactt acagaatcaa aaagactcta tctcaatcct gactcaaaat    2280
gttacctaca ccatctctga catgaatttg cataagaact gttgtttatg ggaatgcatc    2340
ttgatggggc agctgggttg ttatgaaata ctcaggaacc cagcccaggt ctagaattca    2400
cctctgagcg caaaggcaat gttggccatg ctggtaaagg accactagaa tccaggagcc    2460
tggacccctt tctttgtggt caagaaaggc gggaaaacag gtgcaggact gctacatcag    2520
agagcataac aaatccgata agcagagttc catgagtggt aagcaccct ggaaaggaac    2580 tcacctctga gtgcaaaggc aatgttaggc acaccagtaa aggaccacta gaatccagca    2640
gcccagaccc ctttctttgt gatcaagaaa ggcgggaaaa ggggtgcagg actgctacat    2700
cagtgagcgt aactaatctg ataagcagaa gtccatgggt ggttacgcac cctggaaagg    2760 ataagcatt aggaccacag aggacactct aagactaatg ctcattggaa aatgactagg    2820
ggtgctggca tccctatgtt tttttttcag atgggaaaca ttcccccaa ggcaaaaacg    2880 cccataagat atattctgga gaattcggcc cagagtgtat gtatcttttt tccctgtcag    2940
acttgaagca aacctaggta aattatcaga tagccctgat ggctatattg atgctttaca    3000
agggttagga caatccttttg atctaacatg gagagatata ctgttactgc tagatcagac    3060
actaatccca aatgaaagaa gtgccaccat aactgcagcc agagagtttg atgatctctg    3120
gtatctcagt caggtcaatg ataggatgac aacagaagaa agaaaacaat tccccacagg    3180
ccagcaggca gttcccagcg tagaccttca ttgggacaca gaatcagaac atggagattg    3240
gtgccgcaga catttactaa cttgcgcgct agaagcacta aggaaaacta ggaagaagcc    3300
```

```
tatgaattat tcaatgatgt ccactataac acagggaaag gaagaaaatc ctactgcctt      3360
tctggagaga ctaagggagg cattgagaaa gcatacctct ctgtcacctg actctattga      3420
aggccaacta atcttaaagg ataagttttc cactcagtca gctgcagaca ttagaaaaaa      3480
acttcaaaag tctgcgttag gccgggagca aaacttagaa accctattga acttggcaac      3540
ctcagttttt tatgatagag atcaggagga tcaggtggaa tggacaaatg agattttaaa      3600
aaaaggccac cactttagtc atggccctca ggcaagcaga cttttggacac tctgaaaaag      3660 ggaaaagctg gcaaatcga atgcctaata agacttgctt ccagtgtggt ctacaaggac       3720
actttaaaaa agattgtcca aatagaaata agccaccccc tcgtccatgc tccttatgtc      3780
aagggaatca ctggaaggcc tactgcccca ggggatgaag gtcctctgag tcagaagcca      3840
ctaaccagat gattcagccc caggactcag ggtgccagg gcaagcgcca gcctatgcca       3900
tcaccctcac agagccctgg gtatgcttga ccattgaggg tcaggaggtt aactatctcc      3960
tggacactgg cgtggccttc tcagtcttac tctcctgtcc cggacaactg tcctccagat      4020
ctgtcactat ccgagggttt ctacgacagc cagccactag atacttctcc cagccactaa      4080
gttgtgactg gggaactcta ctcttttcac atgttttct aattatgcct gaaagcccca       4140
ctcctttgtt agggaaagac attctagcaa aagcaggggc cattatacac ctgaacatag      4200
gagaaggaac acctgtttgt tgtccctgc ttgaagaagg aattaatcct gaagtctgga       4260
caacagaagg acaatacaga tgagcaacaa atgcctgtcc tgttcaagtt aaactaaagg      4320
attatgcctc cttccctac caaaggcagt accccttag acccgaggcc caacaaggac        4380
tccaaaagat tgttaaggac ctaaaagctc aaagcctagc aaaaccatgc agtagcccct      4440
gcaatactcc aattttagga gtacagaaaa ccaacagaca gtggaggtta gtgcaagatc      4500
tcaggattat caatgaggct gttgttccta acccttatac tctgctttcc caaataccag     4560
aagaagcaga gtggtttaca gtcctggacc ttaaggatgg cttttttctgc atccctgtac    4620 atcctgactc tcaattcttg tttgcctttg gagatccttc gaacccaatg tctcaactca     4680
gcttgactgt tttaccccaa gggttcaggg atagcccca tctagttggc caagcattag      4740
ccgagccagt tctcctacct ggacactctt gtcctctggt acatggatga tttatttta     4800 gctgcccgtt cagaaacctt gtgccatcaa gccacccaag tgctcttaaa tttcctcgcc    4860
acctgtggct acaaggtttc caaaccaaag gctcagctct gctcacagca ggttaaatac   4920
ttagggctaa aattatccaa aggcaccagg gccctcagtg aggaatgtat ccagcctgta   4980
ttggcttatc ctcatcccaa aaccctaaag caactaagag ggttccttgg cataacaggt   5040
ttctgccaaa tgtggattcc caggtacggt gaaatagcca ggccattata taccctaatt   5100
aaggaaactc agaaagccaa cacccatttta ttaagatgga cacctgaagc agaagcagct   5160
ttccaggccc taagaaggc cctaacccaa gccccagtgt taagcttgcc aacggggaag   5220
acttttcttt atatgtcaca gaaaaaacag gaatagctct aggagtcctt agacaggtcc   5280
aagggatgag cttgcaacct gtggcatacc tgagtaagga aattgatgta gttgcaaagg   5340
gttgacctca ttgtttacag gtagtggcgg cagtagcagt cttagtatct gaagcagtta   5400
aaataataca gggaagagat cttactgtgt ggacatctca tgatgtaaac ggcgtactca   5460
cttctaaagg agacttgtgg ctgtcagaca accgtttact taaatatcag gctctattac   5520
ttgaagggcc agtgctgcga ctgcccactt gttcaactct taaccagcc acatttcttt    5580 cagacaatga agaaaagata gaacataact gtcaacaggt gattgctcaa acctacggcg   5640
ctcgagggga ccttctagag gttcccttga ctgatcccaa cctcaacttg tatactgatg   5700
```

```
gaagctcctt tgtagaaaaa ggactttgaa aggtggggta tgcagtggtc agtgataatg    5760
gaatacttga aagtaattcc ttcactccag gaactagtgc tcagctggca gaactaatag    5820
ccctcactca ggcactagaa ttaggagaag gaaaagggt aaatatatat gcagactcta     5880
agtatgctta cccagtcctc cacgcccaca cagcaatatg gagagatagg aaattcctaa    5940
cttctgaggg aacaccgatc aaacatcagg aagccattag gagattatta ttggctgtac    6000
agaaacctaa agaggtggca gtcttacact gctggggtca tcagaaagga aaggaaaagg    6060
aaatagaaag gaaccaccaa gtggatattg aagccaaaag agccacaagg caggccctcc    6120
attagaaatg cttatagaag gatccctagt atggggtaat cccctccggg aaaccaagcc    6180
ccagtactca gcaggagaaa tagacacgag gacatagttt cctcccctca ggatggctag    6240
ccaccgaaaa agggaaaata cttttgcctg cagctaatca atggaaatta cttaaaccc     6300 ttcaccaaac ctttcacttg ggcatggata gcatctatca gatggccaat ttattattta    6360
ctggaccagg cctttcaaa actatcaagc agatagtcag ggcctgtgaa atgtgccaaa     6420
gaaataatcc cctgcacttc aagccataca tttcaatccc tgtatcttta acctcctgtt    6480
gtttgtctct tccagactca aagctgtaaa actgcaaatg gttcctcata tggagcccca    6540
gatgcagtcc atgactaaga tctaccacag agccctagac cggcctgtta gcccatgctc    6600
cgatgttgat gacatcaaag gcacaccttc cgaggaaatc tcaactgcac gacccctact    6660
aagccccaat tcagcaggaa gcagttaaga gcagtcgttg gctaacatcc ccaatagtat    6720
gtgggttttc ctgttgagag gggggactga gagacaggac tagctggatt tcctaggcca    6780
actaagaatc cctaagccta gttgggaagg tgaccgcatc cacctttaaa cacggggctt    6840
gcaacttagc tcacacccga ccaatcaggt agtaaagaga gctcactaaa atgctaatta    6900
ggcaaaaaca agaggtaaag aaatagccaa tcatctatcg cctgagagca cagtggggag    6960
ggacaatgat cgggatataa acccaggcat tcgggccggc aacggcaacc cccattgcgt    7020
cccctcccat tgtatgggag ctctgttttc attctattaa atcttgcaac tgcacactct    7080
tctggtctat gtttgttatg gctcgagctg agctttcgct cgctgtccac cactgctgtt    7140
tgccgccatc gcagacccac cactgacttc cacctctgca gatctggcag ggtgtccgct    7200
gtgctcctga cccagcgagc cacccattgc tgctcccaat caggctaaag gcttgccatt    7260
gttcctgcat ggctaagagc ccagggttcg tcctaatcga gctgaacgct agtagctggg    7320
ttccacagtt ctcttccgtg acccacggct cctaatagag ctataacact caccacatgg    7380
cccaaggttc cattcattgg aatccgtgag gccaagaacc cccggtcaga gaacaagaag    7440
cttgccacca tcttggaagc tctaaaaaca gagacacccc agtaaca                 7487

<210> SEQ ID NO 10
<211> LENGTH: 5470
<212> TYPE: DNA
<213> ORGANISM: Homo sapiens

<400> SEQUENCE: 10
tgagagacag ctggatttcc taggccgact aagaatccct aagcctagct gggaaggtga     60
ccgcatccac ctttaaacac aggggcttgca acttagctca cacccaacca atcagagagc    120
tcactaaaat gctaattagg caaaaacagg aggtaaagaa atagcaagtc atctattgcc    180
tgagagcaca gtgggaggga caaggaccag gatataaacc caggcatttg agccagcaac    240
ggcaacctcc tttgagtccc ctccctttgt ataggagctc tgttttcact gtgtttcact    300
```

```
ctattaaatc ttgcaattgc actcttctgg tccatatttg tcacggcttg agctgagctt      360
tcacttgccg tccaccacta ctgtttgctg ctgtcacaga cccgccgctg actcccatcc      420
cgctgctgac tcccatccct ccggatccgg cagggtgtcc gctgtgctcc tgatccagca      480
agactcccat tgccactccc gatagtgcta aaggcttgcc attgttcctg catggctaag      540
tgcctgggtt cgtcctaatc cagctgaaca ctagtcactg ggttccacgg ttctcttcca      600
tgacccgcgg cttctaatag agctataaca ctcaccacat ggcccaatat tccattcctt      660
ggaatccgtg aggccaagaa ccccaggtca gagaacacga ggcttgccac catcttggaa      720
gcagcctgcc accatcttgg aagtggctca ccaccgtctt gggagttctg tgaacaagga      780
cccctggtaa cattttggcg accacgaagg gacatccaaa gctgtgagta atattggacc      840
actttcgctt gctattctgt tctatcctta gaactggagg aaaatactgg gcacctgtcg      900
ccagttaaaa atgattagca tggccgccgg acttaagact caggtgtgag gctatctggg      960
aaagggcttt ctaacaaccc ccaagccttc tgttgggaac tttggtctgc ctggagccag     1020
cttccacttt caattttctt ggggaagcca agggctgact ggaggcagaa agctgttgtc     1080
ccgaactccc ggcagtagcc ggttgagatc atggcgcagc cagaagtctc tactcggcag     1140
tcgcccatgc gtgcgccctt accttttcctt ctgaattata cctccggggt cccgactccg     1200
actttcttga gagtttagcc ccaaaattct ccttacctct gaatctactt cctttgatcc     1260
ctgcctcctg cctcctaggt actaatagtt cagactttca tttcctctag caagttgtgt     1320
ctccaaaggg atctaaggag gctctatgct gtgtccttag gcacctaggc tataacccag     1380
ggagtcttat ccctggtatc cctcccgatt taggtataca gctcttgaca tgggcagtta     1440
tgtgggacct gttccccacc acccttgtga gggccccaag tttgtaatgg ctaagaaaga     1500
gagacggaga gagagagaga cggagaaaga gacaaagagg gagtcaaaga gaaaagaaa      1560 gaaaagata gaaatagtta aaaaaaaaaa aaagtgtgcc ctattccttt aaaagccagg     1620
gtaaatttaa aacctgtaat tgataattgc cactttgttg tcagtgtaaa taagggcgta     1680
gcaaatcctt aacccagtaa cccgcggata ggccaaatgc attcagtcgg tagcggcaac     1740
agctttgcta aaagtagaaa agtaacttttt agaggaaacc tcattgtgag cacacctcac     1800
cagttcagag ttattctaag taaaaaaaaa aaaaaaaaa aaagcaaaaa ggtagcttac      1860
taactcaata atcttaaagt atggggctac tatgctagaa aagggtaatg taactccaac     1920
cactgataac tcccttaacc cagcagattt cctaacaggg gatttaaatc ttaattacca     1980
cacgaaggtc cgaccagacc taggaggaac tcccttcagc acaggacgat agatggttcc     2040
tcccaggtga ctgaggaaaa aactacaatg ggtattcagt aattggtatg gagactcttg     2100
tggaagcaga gttaaaaatt tgcctaataa ttggtctcct caaatgtgcg agctgtttgc     2160
actcagccaa gccttaaagt acttacagaa tcaaaagact atctcaatcc tgactcaaaa     2220
ggttagctac acagtctctg aaatgaattt gcagaagaac tgttgtttat gggaatgcat     2280
cttgatgggg cagctgggtt gttatgaaat actcaggaac ccagcccagc tctaggactc     2340
accgctgagc gcaaaggcaa tgttgggcac gctggtaaag gaccactaga atccagcagc     2400 ccaggccccct ttctttgtgg tcaagaaagg caggaaaagg agtgcagaac tgctacattg     2460
gtgagcgtaa ctaatccaat aagcagaggt ccatgagtgg ttatgcacgc tggaaaagaa     2520
taagcattag gccctagag gatgctctag gactaatgct catcggaaaa tgactagggg     2580
tgctggcatc cttatgttct ttcttcagat gggaaacgtt ccccccaagg caaaagcgcc     2640
cctaagatgt attctggaga attagaacca atttgaccct cagatgtcaa gaaagaaacg     2700
```

```
acttatattc ttctgcagta ctgcctggcc acgatatcct cttcaagggg gagaaacctg   2760
gcctcctgag ggaagtacaa attataacac catcttacag ctagacctct tttgtagaaa   2820
agaaggcaaa tggagtgaag tgccatatgt gcaaactttc ttttcattaa gagacaactc   2880
acaattatgt aaaaagtgtg gtttatgtct tacaggaagc cctcagagtc tacctcccta   2940
tcccagcatt cccccgactc cttccccaac taataagcac cacccttgaa cccaaacagt   3000
ccaaaaggag atagacaaac aggtaaacaa tgaaccaaag agtgtcagta ttccccgatt   3060
atgccccttc caagcagtgg gaggaggaga attcggccca gccagagtgc atgtaccttt   3120
ttctctctca gacttaacgc aaattaaaat agacttaggt aaattctcag ataaccctga   3180
tggctacatt gatgttttac aagggttagg gcaatccttt gatctgacat ggagagatat   3240
aatgttactg ctaaatcaga cactaacccc aaatgagaga agtgccgccg taactgcagc   3300
ccgagagttt ggtgatctct ggtatctcag tcaggtcaat gataggatga caacagagaa   3360
aagagaacga ttccccacag gccagcaggc agtttccagt gtagaccctc attaggacac   3420
agaatcagaa catggagatt ggtgccacag atatttgcta acttgagtgc tagaaggact   3480
aaggaaaact aggaagaagc ctatgaatta ttcagtgatg tccactataa cacaaggaaa   3540
ggaagaaaat cctactgcct ttctggagag agtaagggag gcattaagga agcataccte   3600 cctgtcacct gactctattg aaggccaact aatcttaaag gataagtttg tcactcagtt   3660
agctgcagac attagaaaaa aacttcaaaa gtccgactta ggcctggagt acggctgagt   3720
gcccaatttg gcagcaggca agaccaacac tgagcccttc atatggcacc atgctttgtg   3780
gtgatcagcc aactacttga tggcaggttg attatattgg acatctttca tcagagaaat   3840
ggcagtggtt tgtccttcct ggaatagaca cttattctcg atatgggttt gtctatcctg   3900
caggcaatgc ttctgccagg agtaccatct gtggactcat ggaaagcctt atccaccatc   3960
atggcattcc acacagcatt gcctctaaac aaggcactta ttttatagct aaggaagtgt   4020
ggcagtgggc tcatgctcat ggaattcact gattgtatct tgttgcccat tatcttaaag   4080
cagctggatt gatagaacag tggaaaggcc atttgaaatc acaattacac caccaactag   4140
gtgacaatac tttgcagggc tcggcaaagt tctcttgaag gctgagtatg tcctgaatca   4200
gcatccaata tatggtactg tttccctcat agccagcatt cacaggccta agaatcaagg   4260
ggtagaagta gaagtggcac cactcaccat cactcctagt gacccactag caaaaatttt   4320
acttccagtt cccccaacat tatgttctgc tggccttagt tccagaggga gaattctgc   4380 caccagtcga cacaagaatg ataccattaa actgaaagtt aaaattgcca cctggccact   4440
ttgggctcct cccacctcta agtcaacagg tcaagaaagg agttacagtg ttgacttggg   4500
tgattgacct ggactatcaa gatgaaatca ggttactact ccacagtgga ggtaaggaag   4560
aatatgtgtg gaatacagga gatcccttag gccgtctttt agtactacca tgccctgtga   4620
ttaaggtcag tggaaaacta caacaatcca atctaggcag gactacaaat ggcccagact   4680
cttcaggaat gaagggttgg gtgacttcac caggtaaaaa aataacagcc tgctgaggtg   4740
ctagctgaag gcaaagggaa tacagaatgg ttagtagaaa aaggtagtca tcaataccag   4800
ctatgaccac aagaccagtt gcagaaatga gacctgtaat tgtcatgtgg atttcctcct   4860
tacatgtttg tgcatgtata cacttctact aagaaaatac ctttatttat ttcctttgct   4920
tttcccttat caagtgacat tattaacttc atatcagcag ttaagtgtta ttaactttat   4980
gtaatagcat ttcggttaat aattcacttc tggttgtatg aaggatagcc gtattaagtt   5040
```

```
aggtgtaatt atgacatcat tattgtcttt atttgaagat tatgtgtaat ttcaggagat      5100
gtgtatgggt tcaagttgac aagggatgga cttgtgatgg ctaatgttga gtgtcaactt      5160
gactgaggat gcaaagtatt gttcctgggt gtgtctgtga gggtgttgcc aaaggagatt      5220
aacatttgtg tcagtgaact gggagatgca gacccacccg caatctgggt gagcaccatg      5280
taatcagctg ccagagcagc tagaataaag caagcagaag aaggtggaag gagctgactt      5340
gctgagtctt ctagtattct tcgttcttct atgctggttg cttcctgccc ccaaacatca      5400
gtctgcaagt tcttctgctt ttggactctt ggacttacac cagtggtttg ccagggactc      5460
tcgggccttc                                                            5470

<210> SEQ ID NO 11
<211> LENGTH: 783
<212> TYPE: DNA
<213> ORGANISM: Homo sapiens

<400> SEQUENCE: 11
tgagagacag gactaactgg atttcctagg ccgactaaga atccctaagc ctagctggga        60
aggtgaccgc atccatcttt aaacacgggg cttgaaactt agctcacacc taaccagtca       120
gagagctcac taaaatgcta attaggcaaa aaacaggagg taaagaaata gccaatcatc       180
tattgcctga gagcacagcg ggagggacaa ggatcgggat ataaacccag gcattcgagc       240
cagcaatggc aaccccttt gggtcccctt cccttgtatg ggagctctgt tttcactcta       300
tttcactcta ttaaatcttg caactgcact cttctggtcc atgtttgtta cggctcgagc       360
tgagctttgg ctcgccatcc accactgctg tttgccgccg tcgcacacct gctgctgact       420
cccatccctc cggatccagc agggtgtgtc cgctgtgctc ctgatccagc gaggtgccca       480
ttgccgctcc tgattggact aaaggcttgc cattgttcct gcacggctaa gtgcccgggt       540
tcgtcctaat ccagctgaac actagtcact gggttccacg gttctcttcc ttgacccacg       600
gcttctaata gagctataac actcaccgca tgggccaaga ttccattcct tggaatctgt       660
gaggccaaga accccaggtc agagaacacg aggcttgcca ccatcttgga agcggcctgc       720
caacatcttg gaagtggctc gccaccatct tgggagctct gtgagcaagg acccctggta       780
aca                                                                   783

<210> SEQ ID NO 12
<211> LENGTH: 7542
<212> TYPE: DNA
<213> ORGANISM: Homo sapiens

<400> SEQUENCE: 12
tgagagacag gactagctgg atttcctagg ccgactaaga atccctaagc ctagctggga        60
aggtgaccgc ttccaccttt aaacacgggg cttgcaactt agctcacacc cgaccaatca       120
gatagtaaag agagcacact aaaatgctaa ttaggcaaaa acaggaggta agaaatagc        180 caatcatcta ttgcctgaga gcaaagcggg agggacaatg atcgggatag aaacccaggc       240
attcaagccg gaatggctac cctctttggg tcccctccct tgtatggga gctctgtttt       300 cactctattc aatcttgcaa ctgcactctt ctggtccgtg tttgttacag cttgagctga      360
gctttcgctc gccttccacc actgctgttt gccgccatcg cagacctgcc gtgctgactt       420
ccatccctct agatctggca gggtgtccgg tgtgctcttg atccagcgag gcgcccattg       480
ccgctcccga ttgggctaaa ggcttgcaat tgttcctgca cgctaagtgc ctgggttcat       540
cctcatcaag ctgggttcca cggttctctt catgacccgc agcttctaac agagctataa       600
```

```
aactctgtgc atggcccaag attccattcc ttggaatctg tgaggccaag aaccccaggt    660
cagagaacag gaggcttgcc accatcttgg aagtggctcg ccaccatctt aggagctctg    720
tgagcggaga ccccccacccc ccggtaacat tttggcgacc acgaagggac ctccaaagcg    780
gtgagtaata ttgatcact  ttcgcttgct attctgtcct atccttcttt agaattggag     840
gaaaatactg ggcacctgtc ggccagttaa aaacaattag cgtggctgcc cgacttaaga    900
ctcaggtgtg aggctatctg ggaagggct  ttctaacaac ccccaaccct tctgggttgg     960
ggacgttggt ctgcccttc  cactttcaat tttcttgggg aagccaaggg tcgactagag    1020
gcagaaagct gtcgtccgga actcctggca gtagccggtt gagatcatgg cgcagccaga   1080
agtctctact caacagtcgc ccatgcgtgc gctcctacct ttcctcctga cccatacctc    1140
ctgggtcccg acgatgactt tcttgaaagt gtagccccaa aattctgctt acctctgaat    1200
ctacttcccc tgatccctgg ctcctaggta ctaatggttc agtttcattt cctctagcaa    1260
gttgtatctc caaagggatc taaggaagct ctacgctgcg tccttaggca tctaggctat    1320
aaacccagga agtcttgtcc ctggtgtccc tcccgattta ggcatacagc tctcgacatg    1380
ggcagttatg tgggacccgt tccccatcac ccttgtcaag gccccaagtt tgtaatggct    1440
aagaggagag agagagaaag agagagagac ggagggagaa gagagagaga gagatggagg    1500
ggagagagag agagagagac ggagggagaa gagagagaga gagagagacg gaggggagag    1560
agagagagac ggaggggaga gagagagaga tggaggagag aaagacaaag ggagtcaaag    1620
agaaaaagaa agagaaagac agaaatggta aaacaaacaa aaaacagcgt gccctattcc    1680
tttaaaagcc ggggtaaatt taaaacctat aattgataat tgaaggtctt ctccatgacc    1740
ctataatact ccaatactac cttgttgtca gtgtaaacaa gggcgtagcc tgaaaacact    1800
gagaccactg acaacctgca gctttcctat caaaaaatcc ttaacccagt aaccggcaga    1860
tgcattcaat ctgtagcagc aactgttttg ctaacagaag aaagtagaaa agtaactttt    1920
agaggaaacc tcattgtgag cacaccttac cagttcagaa ttattctaag tcaaaaaagc    1980
aaaaaggtag cttactaact caaaaatctt aaagtatggg gctattgtgt ttaaaaaaaa    2040
aaaaaggtaa tttaacacca accactgata attctcttaa cccagcaggt ttcctaacag    2100
gggatttaaa tcttaattac catacaaagg tctgaccaca cctaggagga actcccttca    2160
ggacaggact atagagggtt cctcccaggt gattgaggaa aaaaccacag tgggtattca    2220
gtaattgata gggagactct tgtggaagca gagttagaaa aattgcctaa taaatggtgt    2280
cctcaaaagt gtgagctgtt tgcactcagc caagccttaa agtacttaca gaatcgtaaa    2340
aactatctca atcctgactc aaaagtttac ttacaccctc tctgaaatga atttacataa    2400
gaactgcttt tttgggaatg catccttgatg gggcagctgg gtggttatga aatactcagg    2460
aaaccagccc agctctagga cacatccctg agcacaaagg caatgttggg cacgctggta    2520
aaggaccact agaatccagc agcctggact cctttctttg tggtcaagaa aggcaggaaa    2580
acaggtgcag gactgctaca tcagtgagca taactaatct gataagcaga gggccttggg    2640
tggttacaca ccctggaaag gaattcaact ctgagcgcaa aggcaatgtt gggcacattg    2700
gtaaaggacc actagaatcc agcagcccag gcccctttct ttatggtcaa gaaaggcggg    2760
aaaaggggtg caggactgtt acctcggtga gcgtaactaa tccgataagc agaggtccat    2820
gggtgattac gcaccctgaa aagaataagc attaggccct taaaggatgc tctaggacta    2880
atgctcattg gaaaatgact aggggtgctg gcatccctat gttctttcct cagacgggaa    2940
```

```
atgttctcca ccctccccaa ggcaaaaaca cccctaagat gtattctgga gaattgggac    3000
caatttgacc cccagacgct aagaaagaga tgacttatgt tcttctgcag taccacctgg    3060
ccacgatatc ctcttcaagg gggagaaacc tggcctcctg agggaagtat aaattataac    3120
accatcttac agctagacct cttctgtaga aaggagggca aatggagtga agtgccatat    3180
gtgcaaactt tcttttcatt aagagacaac ttgcaattat gtaagaagtg tgatttatgc    3240
cctacaggaa gccctcagag tctacctccc tacccagca tccccctgac tccttctcca     3300
actaataagg aaccccttc aacccaaacg gtccaaaagg agatagacaa aggggtaaac     3360
aatgaaccaa agcgtgccaa tgttccctga ttatgccccc tctaagcagt gggaggagga    3420
gaatttggcc cagccagtgt gcatgtgcct ttttctctct cagacttaaa gcaaattaaa    3480
atagacctag gtaaattctc agataaccct gatggctata ttgatgtttt ataagggtta    3540
ggataatcct ttgatctgac atggagagat ataatgttac tgctagatca gacactaacc    3600
ccaaatgaga caagtgccgc cataactgca gcctgagagt ttggcgatct ctggtatctc    3660
actcgggtca atgataggag gacaacagag gaaagagaat gattccccac agaccagcag    3720
gcagttccca gtgtagaccc tcactgggac acagaatcag aacatggaca ttggtgctgc    3780
agacatttgc taacttacat gctagaagga ctaaggaaaa ctaggaagaa gcctacgaat    3840
tattcaatga tgtccactat aacacaggga aaggaagaaa atcctactgc ctttctggag    3900
cgactaaggg aggcattgag gaagcatact tccctgtcac ctgactctat tgaaggccaa    3960
ctaatcttaa aggataagtt tatcactcag tcagctgaag acattaggaa aaaacttcaa    4020
aagtctgcct taggcccaga gcaaaactta gaaaccccat tgaacttggc aacctcggtt    4080
ttttataata gagatcagga ggagcaggcg gaacaggaca aacggggtaa aaaaaaggcc    4140
accgctttag ttatggccct caggcaagtg gactttggag gctctggaaa agggaaaagc    4200
tgggcaaatc gaatgcctac tagggcttgc ttccagagtg gtctacaagg cactttgaa     4260 aaagattgtc caagtagaaa taagtcgccc cttcgtccat gcccctatta tcaagggaat    4320
cactggaagg cccactatcc caggggacaa atgtcctctg agtcagaagc cactaaccag    4380
atgatccagc agcaggactg agggtgccca gggcaagcac tagcccatgc cgtcaccctc    4440
acagagcccc aggtatgctt gaccattgag ggccaggagg ttaactgtct cctggacact    4500
agcacggcct tctcagtctt actctccttt cccggacaac tgtcctccag atctgtcact    4560
atccgagggt tcctaggaca gtcagtcact agatacttat cccagtcact aagttgtgac    4620
tggtgaactt tactcttttc acatgctttt ctaattatcc ctgaaagcac cactcccttg    4680
ttagggcgag acattctagc aaaagcaggg gccattatac acctgaacat aggagaagga    4740
acacctgttt gttgtcccct gcttgaggaa ggaattaatc ccgaagtctg ggcaacagaa    4800
ggacaatacg gacgagcaaa gaatgcctgt gctgttcaag ttaaactaaa ggattccgcc    4860
tcctttccct accaaaggca gtaccccctt agacctgagg cccaacaagg actccaaaag    4920
attgttaagg acctaaaagc ccatggccta gtaaaaccat gcaatagccc ctgcaatact    4980
ccaattttag gagtacagaa acccaacaga cagtggaggt tagtgcaaga tctcaggatt    5040
atcattgagg ctgttgttcc tgtatagcca gctgtaccta accttatac tctgctttcc     5100 caaataccac aggaagcaga ggggtttaca gtccggggcc ttaaggacac ctttttctgc    5160
atccctgtat atcctgactc tcaattcttg tttgcctttg aagatccttc aaactcaacg    5220
tctcaactca cctggaatgt tttacccaa ggggttcaggg atagccccca ttagcccaag    5280
acttgagcca gttcttatac ctggacactc ttgtcctttg gtacgtggat gatttacttt    5340
```

```
tagccacctg ttcagaaacc ttgtgccatc aagccaccca agcactcttt aatttcctcg    5400
ccacctgtgg ctacaggttt ccaaaccaaa ggctcagctc tgctcacagc aatttaaatg    5460
cttagggcta aaattatcca aaggcaccag ggccctcagt gaggaaagta tccggcctat    5520
actggcttat cctcatccca aaaccctaaa gcaactaaga gtgttccttg cataacggg    5580 tttctgccga atatggattc ccaggtacag cgaaatagcc agaccattat atacactaat    5640
taaggaaact cagaaagcca atacccattt ggtaagatgg acacctgaag cagaagcaga    5700
tttccaggcc ctaagaagg ccctgaccca gccccagtg ttaagcttgc caatggggca     5760 agactttct ttatatgtca cagaaaaaac aggaatagct ccaggagtcc ttacgcagat    5820
ccaagggacg agcctgcaac ccatggcata cctgagtaag gaaattagtg caaagggtt    5880 ggcctcattg tttatgggta gtggcagcag tcacagtctt agtaactgaa gcagttaaaa    5940
tgatacaagg aagagatctt actgtgtgga catctcatga tgtgaatggc atactcactg    6000
ctaaaggaga cttgtgactg tcagacaact gtttacttaa atatcaggct ctattacttg    6060
aagggccagt gttgcgactg tgcacttgtg caactcttaa cccagccaca ttgcttccag    6120
acaatgaaga aaagatagaa cataactgtc aacaaataat tgctcaaacc tacactgctc    6180
gaggggacct tttagaagtt cccttgactg atcccgatct caacttgtat actgatggaa    6240
gttcctttgc agaaaaagga cttcaaaagg cggtgtatgc agtagtcctt caaaatcgaa    6300
gagctttaga attgctaatc actgagagag ggggaacgtt tttattttta ggggaagaat    6360
gctgttatta tgttaatcaa ttcggaatca tcaccaagaa agttaaagaa attcaagatc    6420
gaatacaacg tagaacagag gagcttaaaa aacactggac cctggggcct cctcagccaa    6480
tggatgccct ggattctccc cttcttagga cctctagcag ctatatttct actcctcttt    6540
ggaccctgta tctttaacct ccgtgttaag tttgtctctt ccagaatcga agatgtaaaa    6600
ctacaaatcg ttcttcaaat ggaccccag atgcagtcca tgactaagat ctactgagga     6660
cccctggacc agcctgctag cccatgctcc aatgttaatg acattgaagg cacccctccc    6720
aaggaaatct caactgcaca ccccctacta tgctccaatt cagcaggaag cagttacagt    6780
ggtcctcggc caacctcccc aacagcattt gtattttcct gttgggaggg ggcactgaga    6840
gacaggacta gctggatttc ctaggctgac tgagaatccc taagcctagc tgggaaggtg    6900
accacttcca ccttttaaaca cagggcttgc aacttagctc acaccctacc aattggatag    6960
taaagagagg tcactaaaat gctaattagg caaaaacagg aggtaaagaa atagccaatc    7020
atccattgcc tgagagcaca gcgggaggga caatgaccag gatataaacc caggcattcc    7080
agcctgcaac ggcaaccccc tttgggtccc ctctctttgt atgggagctc tgttttcact    7140
ctattcaatc ttgcaactgc actcttctgg tccgtgtttg ttacggctca agctgagctt    7200
ttgctcacca tccaccactg ctgtttgccg ccgttgcaga cccgtcgctg acttccatcc    7260
ctccagatct ggcagggtgt ccactgtgct cctgatccag cgaggcaccc attgccactc    7320
ccgatcaggc taaaggcttg ccattgttcc tgcacagcta agtgcctggg ttcgtcctaa    7380
tcaagctgaa cactagtcac tgggttccat ggttctcttc catgacccat ggcttctaat    7440
agagctataa cactcaccgc atggcccaag attccattcc ttggaatccg tgaggccaag    7500
aaccccaggt cagagaacac gaggctgccg ccatcttgga ag                       7542
```

<210> SEQ ID NO 13
<211> LENGTH: 10288
<212> TYPE: DNA

<213> ORGANISM: Homo sapiens

<400> SEQUENCE: 13

| | |
|---|---|
| cctgggcgg gcttcctttc tgggatgagg gcaaaacgcc tggagataca gcaattatct | 60 |
| tgcaactgag agacaggact agctggattt cctaggccga ctaagaatcc ctaagcctag | 120 |
| ctgggaaggt gaccacgtcc acctttaaac acggggcttg caacttagct cacacctgac | 180 |
| caatcagaga gctcactaaa atgctaatta ggcaaagaca ggaggtaaag aaatagccaa | 240 |
| tcatctattg cctgagagca cagcaggagg gacaacaatc gggatataaa cccaggcatt | 300 |
| cgagctggca acagcagccc ccctttgggt cccttccctt tgtatgggag ctgttttcat | 360 |
| gctatttcac tctattaaat cttgcaactg cactcttctg gtccatgttt cttacggctc | 420 |
| gagctgagct tttgctcacc gtccaccact gctgtttgcc accaccgcag acctgccgct | 480 |
| gactcccatc cctctggatc ctgcagggtg tccgctgtgc tcctgatcca gcgaggcgcc | 540 |
| cattgccgct cccaattggg ctaaaggctt gccattgttc ctgcacggct aagtgcctgg | 600 |
| gtttgttcta attgagctga acactagtca ctgggttcca tggttctctt ctgtgaccca | 660 |
| cggcttctaa tagaactata acacttacca catgcccaa gattccattc cttggaatcc | 720 |
| gtgaggccaa gaactccagg tcagagaata cgaggcttgc caccatcttg gaagcggcct | 780 |
| gctaccatct tggaagtggt tcaccaccat cttgggagct ctgtgagcaa ggacccccg | 840 |
| gtaacatttt ggcaaccacg aacgacatc caaagtggtg agtaatattg gaccactttc | 900 |
| acttgctatt ctgtcctatc cttccttaga attggaggaa aataccgggc acttgtcggc | 960 |
| cagttaaaaa cgattagtgt ggccaccgga cttaagactc aggtgtgagg ctatctgggg | 1020 |
| aagggctttc taacaacccc caaccccttct gggttgggga cttggtttgc ctcaagccag | 1080 |
| cttccactt cagttttctt ggggaagccg agggccgact agaggcagaa agctgtcgtc | 1140 |
| ctgaactccc ggcagtagcc ggttgagatc atggtgtagc cagaagtctc aacagtcgcc | 1200 |
| catgcatgca cccctatctt ccttctgac ccataccttcc tgggtcccaa ccacaacttt | 1260 |
| cttcaaagtg tagccccaaa attctcctta cctctgaata tacttcctct gatccctgcc | 1320 |
| tcctaggtac tattggttca gacttccatt tcctctagca agttgtatct ccaaagggat | 1380 |
| ctaaggaagc tctgcgctgc gtccttaggc acctaggcta taacccaggg agtcttatcc | 1440 |
| ctggtgtccc tcccaatta ggcatacagc tcttgacatg ggcagttatg taggaccac | 1500 |
| tccccaccac ccttgccagg gccccaagtt tgtaaatggc tgagggaaaa gagagacaga | 1560 |
| ggagagagag agaaatggag gagaaagaga gagacaga gaggagagag agacagtgag | 1620 |
| agagacagaa gagagagaga gacaaagagg agagagagag agtcaaagag agaaagaaag | 1680 |
| agaaagaaat agtaaaaaac agtgtgccct attcctttaa aagccagggt aaatttaaaa | 1740 |
| cctgtacttg ataattgaag gtcttctctg tgaccctata gcactccaat ccactttgtg | 1800 |
| gtcagtgtaa ataagagcat aggccgaaag cactgaggcc attgacaacc cgtagcttcc | 1860 |
| ctatcaaaaa tccttaaccc agtaacccgc agatggacca aatgcattca gtcggtagcg | 1920 |
| caactgcttt gctaaagta gaaagtaac ttttagagga aacctcattg tgagcacacc | 1980 |
| tcacctgttc agaattattc taataaaaaa agcaaaagg tagcttacta actcaaaat | 2040 |
| cttaaagtat ggggctattc tgttagaaaa aggtaatgta actccaacca ctgataattc | 2100 |
| ccttaaccca gcagatttcc taacgggatt taaatcttaa ttaccataca aaggtccgac | 2160 |
| cagacctagg cggaactccc ttcaggacag gacgatagat ggttcctccc aggtgattga | 2220 |
| ggaaaaaaac cacaatgggt attcagtaat tgatacgggg actcttgtgg aagcagagtt | 2280 |

```
agaaaaattg cctaataact ggtctcctca aacgtgtgag ctgtttgcac tcagccaagc    2340
cttaaagtac ttacagaatc aaaagactat ctcaatcctg attcaaaagg ttagctacac    2400
cctctctgta atgcatttgc ataagaactt gtttatggga atgcatcttg atggggcagc    2460
tgggttgtta taaaatagga acccagccca gctctaggac tcacccctga gcgcaaaggc    2520
aatgttgggc atgctggtaa aggaccacta gaatccagca gcccagaccc ctttctttgt    2580
ggtcaagaaa ggcgggaaaa ggggtgcagg actgctacat cggtaagcat aactaatccg    2640
ataaacagag gtccatgggt ggttacgcac cctggaaagg aactcacccc tgagcacaaa    2700
ggcaatgttg gcacgctgg taaaggacca ctagaatcca gcagcctgga ccccttcctt    2760
tgtggtcaag agaggcagga aaacaggtgc aggactgcaa catcagtgag cataactaat    2820
tcgataagca gaggtccatg ggtggtgatg caccctggaa agaataagca ttaggaccat    2880
agaggacact ccaggactaa agctcatcgg aaaatgacta gggttgctgg catccctatg    2940
ttcttttttc agatgggaaa cgttccccgc aagacaaaaa cgcccctaag acgtattctg    3000
gagaattggg accaatttga ccctcagaca ctaagaaaga aacgacttat attcttctgc    3060
agtgccgcct ggcactcctg agggaagtat aaattataac accatcttac agctagacct    3120
cttttgtaga aaaggcaaat ggagtgaagt gccataagta caaactttct tttcattaag    3180
agacaactca caattatgta aaagtgtga tttatgccct acaggaagcc ttcagagtct    3240
acctccctat cccagcatcc ccgactcctt ccccaactaa taaggacccc ccttcaaccc    3300
aaatggtcca aaaggagata gacaaaaggg taaacagtga accaaagagt gccaatattc    3360
cccaattatg acccctccaa gcagtgggag gaagagaatt cggcccagcc agagtgcatg    3420 tgccttttc tctcccagac ttaaagcaaa taaaaacaga cttaggtaaa ttctcagata    3480
accctgatgg ctatattgat gttttacaag ggttaggaca attctttgat ctgacatgga    3540
gagatataat gtcactgcta aatcagacac taaccccaaa tgagagaagt gccaccataa    3600
ctgcagcctg agagtttggc gatctctggt atctcagtca ggtcaatgat aggatgacaa    3660
cagaggaaag agaatgattc cccacaggcc agcaggcagt tcccagtcta gaccctcatt    3720
gggacacaga atcagaacat ggagattggt gctgcagaca tttgctaact tgtgtgctag    3780
aaggactaag gaaaactagg aagaagtcta tgaattactc aatgatgtcc accataacac    3840
agggaaggga agaaaatcct actgcctttc tggagagact aagggaggca ttgaggaagc    3900
gtgcctctct gtcacctgac tcttctgaag gccaactaat cttaaagcgt aagtttatca    3960
ctcagtcagc tgcagacatt agaaaaaaac ttcaaaagtc tgccgtaggc ccggagcaaa    4020
acttagaaac cctattgaac ttggcaacct cggttttta taatagagat caggaggagc    4080
aggcggaaca ggacaaacgg gattaaaaaa aaggccaccg ctttagtcat gaccctcagg    4140
caagtggact ttggaggctc tggaaaaggg aaaagctggg caaattgaat gcctaatagg    4200
gcttgcttcc agtgcggtct acaaggacac tttaaaaaag attgtccaag tagaagtaag    4260
ccgccccctc gtccatgccc cttatttcaa gggaatcact ggaaggccca ctgccccagg    4320
ggacaaaggt cctctgagtc agaagccact aaccagatga tccagcagca ggactgaggg    4380
tgcctggggc aagcgccatc ccatgccatc accctcacag agccctgggt atgcttgacc    4440
attgagggcc aggaggttgt ctcctggaca ctggtgcggt cttcttagtc ttactcttct    4500
gtcccggaca actgtcctcc agatctgtca ctatctgagg gggtcctaag acgggcagtc    4560
actagatact tctcccagcc actaagttat gactggggag ctttattctt ttcacatgct    4620
```

```
tttctaatta tgcttgaaag ccccactacc ttgttaggga gagacattct agcaaaagca   4680
ggggccatta tacacctgaa cataggagaa ggaacacccg tttgttgtcc cctgcttgag   4740
gaaggaatta atcctgaagt ctgggcaaca aaggacaat atggacgagc aaagaatgcc    4800
cgtcctgttc aagttaaact aaaggattcc acctcctttc cctaccaaag gcagtacccc   4860
ctcagaccca aggcccaaca aggactccaa aagattgtta aggacctaaa agcccaaggc   4920
ctagtaaaac catgcagtaa cccctgcagt actccaattt taggagtaca gaaacccaac   4980
agacagtgga ggttagtgca agatctcagg attatcaatg aggctgttgt tcctctatag   5040
ccagctgtac ctagccctta tactctgctt tcccaaatac cagaggaagc agagtggttt   5100
acagtcctgg accttcagga tgccttcttc tgcatccctg tacatcctga ctctcaattc   5160
ttgtttgcct ttgaagatac ttcaaaccca acatctcaac tcacctggac tattttaccc   5220
caagggttca gggatagtcc ccatctattt ggccaggcat tagcccaaga cttgagccaa   5280
tcctcatacc tggacacttg tccttcggta ggtggatgat ttacttttgg ccgcccattc   5340
agaaaccttg tgccatcaag ccacccaagc gctcttcaat ttcctcgcta cctgtggcta   5400 catggttcc aaaccaaagg ctcaactctg ctcacagcag gttacttagg gctaaaatta   5460
tccaaaggca ccagggccct cagtgaggaa cacatccagc ctatactggc ttatcctcat   5520
cccaaaaccc taaagcaact aaggggattc cttggcgtaa taggtttctg ccgaaaatgg   5580
attcccaggt atggcgaaat agccaggtca ttaaatacac taattaagga aactcagaaa   5640
gccaataccc atttagtaag atggacaact gaagtagaag tggcttttcca ggccctaacc   5700 caagccccag tgttaagttt gccaacaggg caagacttt cttcatatgt cacagaaaaa   5760
acaggaatag ctctaggagt ccttacacag atccgaggga tgagcttgca acctgtggca   5820
tacctgacta aggaaattga tgtagtggca aagggttgac ctcattgttt acgggtagtg   5880
gtggcagtag cagtcttagt atctgaagca gttaaaataa tacaggaag agatcttact   5940 gtgtggacat tcatgatgt gaatggcata ctcactgcta aaggagactt gtggctgtca   6000
gacaactgtt tacttaaatg tcaggctcta ttacttgaag ggccagtgct gcgactgtgc   6060
acttgtgcaa ctcttaaccc agccacattt cttccagaca atgaagaaaa gataaaacat   6120
aactgtcaac aagtaatttc tcaaacctat gccactcgag gggacctttt agaggttcct   6180
ttgactgatc ccgacctcaa cttgtatact gatggaagtt cctttgtaga aaaggactt    6240 cgaaaagtgg ggtatgcagt ggtcagtgat aatggaatac ttgaaagtaa tcccctcact   6300
ccaggaacta gtgctcagct agcagaacta atagcctca cttgggcact agaattagga   6360 gaagaaaaa gggcaaatat atatacagac tctaaatatg cttacctagt cctccatgcc   6420
catgcagcaa tatggaaaga aagggaattc ctaacttctg agagacacc tatcaaacat   6480 caggaagcca ttaggaaatt attattggct gtacagaaac ctaaagaggt ggcagtctta   6540
cactgccggg gtcatcagaa aggaaaggaa agggaaatag aagagaactg ccaagcagat   6600
attgaagcca aaagagctgc aaggcaggac cctccattag aaatgcttat aaaacaaccc   6660
ctagtatagg gtaatcccct ccgggaaacc aagcccagt actcagcagg agaaacagaa    6720
tggggaacct cacgaggaca gttttctccc ctcgggacgg ctagccactg aagaagggaa   6780
aatacttttg cctgcaacta tccaatggaa attacttaaa acccttcatc aaaccttca    6840 cttaggcatc gatagcaccc atcagatggc caaatcatta tttactggac caggcctttt   6900
caaaactatc aagcagatag tcaggccctg tgaagtgtgc cagagaaata tcccctgcc    6960 ttatcgccaa gctccttcag gagaacaaag aacaggccat taccctggag aagactggca   7020
```

```
actgatttta cccacaagcc caaacctcag ggatttcagt atctactagt ctgggtagat   7080
actttcacgg gttgggcaga ggccttcccc tgtaggacaa aaaaggccca agaggtaata   7140
aaggcactag ttcatgaaat aattcccaga ttcggacttc cccgaggctt acagagtgac   7200
aatagccctg ctttccaggc cacagtaacc cagggagtat cccaggcgtt aggtatacga   7260
tatcacttac actgcgcctg aaggccacag tcctcaggga aggtcgagaa atgaatgaa    7320
acactcaaag gacatctaaa aaagcaaacc caggaaaccc acctcacatg gcctgctctg   7380
ttgcctatag ccttaaaaag aatctgcaac tttccccaaa aagcaggact tagcccatac   7440
gaaatgctgt atggaaggcc cttcataacc aatgaccttg tgcttgaccc aagacagcca   7500
acttagttgc agacatcacc tccttagcca aatatcaaca agttcttaaa acattacaag   7560
gaacctatcc ctgagaagag ggaaaagaac tattccaccc ttgtgacatg gtattagtca   7620
agtcccttcc ctctaattcc ccatccctag atacatcctg ggaaggaccc tacccagtca   7680
ttttatctac cccaactgcg gttaaagtgg ctggagtgga gtcttggata catcacactt   7740
gagtcaaatc ctggatactg ccaaaggaac ctgaaaatcc aggagacaac gctagctatt   7800
cctgtgaacc tctagaggat ttgcgcctgc tcttcaaaca acaaccagga ggaaagtaac   7860
taaaatcata aatccccatg gccctccctt atcatatttt tctctttact gttcttttac   7920
cctctttcac tctcactgca ccccctccat gccgctgtat gaccagtagc tcccttacc    7980
aagagtttct atggagaatg cagcgtcccg gaaatattga tgccccatcg tataggagtc   8040
tttctaaggg aaccccccacc ttcactgccc acacccatat gccccgcaac tgctatcact   8100
ctgccactct ttgcatgcat gcaaatactc attattggac aggaaaaatg attaatccta   8160
gttgtcctgg aggacttgga gtcactgtct gttggactta cttcacccaa actggtatgt   8220
ctgatggggg tggagttcaa gatcaggcaa gagaaaaaca tgtaaaagaa gtaatctccc   8280
aactcacccg ggtacatggc acctctagcc cctacaaagg actagatctc tcaaaactac   8340
atgaaaccct ccgtacccat actcgcctgg taagcctatt taataccacc ctcactgggc   8400
tccatgaggt ctcggcccaa aaccctacta actgttggat atgcctcccc ctgaacttca   8460
ggccatatgt ttcaatccct gtacctgaac aatggaacaa cttcagcaca gaaataaaca   8520
ccacttccgt tttagtagga cctcttgttt ccaatctgga aataacccat acctcaaacc   8580
tcacctgtgt aaaatttagc aatactacat acacaaccaa ctcccaatgc atcaggtggg   8640
taactcctcc cacacaaata gtctgcctac cctcaggaat atttttttgtc tgtggtacct   8700
cagcctatcg ttgtttgaat ggctcttcag aatctatgtg cttcctctca ttcttagtgc   8760
cccctatgac catctacact gaacaagatt tatacagtta tgtcatatct aagccccgca   8820
acaaaagagt acccattctt ccttttgtta taggagcagg agtgctaggt gcactaggta   8880
ctggcattgg cggtatcaca acctctactc agttctacta caaactatct caagaactaa   8940
atgggacat ggaacgggtc gccgactccc tggtcaccct gcaagatcaa cttaactccc    9000
tagcagcagt agtccttcaa aatcgaagag ctttagactt gctaaccgct gaaagagggg   9060
gaacctgttt atttttaggg gaagaatgct gttattatgt taatcaatcc ggaatcgtca   9120
ctgagaaagt taaagaaatt cgagatcgaa tacaacgtag agcagaggag cttcgaaaca   9180
ctggaccctg gggcctcctc agccaatgga tgccctggat tctcccccttc ttaggacctc   9240
tagcagctat aatattgcta ctcctctttg gaccctgtat cttaaccctc cttgttaact   9300
ttgtctcttc cagaatcgaa gctgtaaaac tacaaatgga gcccaagatg cagtccaaga   9360
```

```
ctaagatcta ccgcagaccc ctggaccggc ctgctagccc acgatctgat gttaatgaca    9420
tcaaaggcac ccctcctgag gaaatctcag ctgcacaacc tctactacgc cccaattcag    9480
caggaagcag ttagagcggt cgtcggccaa cctccccaac agcacttagg ttttcctgtt    9540
gagatggggg actgagagac aggactagct ggatttccta ggctgactaa gaatccctaa    9600
gcctagctgg gaaggtgacc acatccacct ttaaacacgg ggcttgcaac ttagctcaca    9660
cctgaccaat cagagagctc actaaaatgc taattaggca aagacaggag gtaaagaaat    9720
agccaatcat ctattgcctg agagcacagc aggagggaca atgatcggga tataaaccca    9780
agtcttcgag ccggcaacgg caaccccctt tgggtcccct cccttgtat gggagctctg     9840 tttcatgct atttcactct attaaatctt gcaactgcac tcttctggtc catgtttctt     9900
acggcttgag ctgagctttc gctcgccatc caccactgct gtttgccgcc accgcagacc    9960
cgccgctgac tcccatccct ctggatcatg cagggtgtcc gctgtgctcc tgatccagcg   10020
aggcacccat tgccgctccc aatcgggcta aaggcttgcc attgttcctg catggctaag   10080
tgcctgggtt catcctaatt gagctgaaca ctagtcactg ggttccatgg ttctcttctg   10140
tgacccacag cttctaatag agctataaca ctcaccgcat ggcccaaggt tccattcctt   10200
gaatccataa ggccaagaac cccaggtcag agaaacgag gcttgccacc atcttgggag    10260
ctctgtgagc aaggaccccc aagtaaca                                      10288
```

```
<210> SEQ ID NO 14
<211> LENGTH: 18
<212> TYPE: DNA
<213> ORGANISM: Artificial sequence
<220> FEATURE:
<223> OTHER INFORMATION: Synthetic Construct - amplification primer

<400> SEQUENCE: 14
tgcagatgct gtgtctgg                                                      18

<210> SEQ ID NO 15
<211> LENGTH: 17
<212> TYPE: DNA
<213> ORGANISM: Artificial sequence
<220> FEATURE:
<223> OTHER INFORMATION: Synthetic Construct - amplification primer

<400> SEQUENCE: 15
cgtactggcc caggacc                                                       17

<210> SEQ ID NO 16
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 16
ggttcgtgct aattgagctg                                                    20

<210> SEQ ID NO 17
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 17
atggtggcaa gcttcttgtt                                                    20
```

```
<210> SEQ ID NO 18
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 18
tgagctttcc ctcactgtcc                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 19
tgttcggctt gattaggatg                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 20
catggcccaa tattccattc                                              20

<210> SEQ ID NO 21
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 21
ggtccttgtt cacagaactc c                                            21

<210> SEQ ID NO 22
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 22
ccgctcctga ttggactaaa                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 23
cgtgggtcaa ggaagagaac                                              20

<210> SEQ ID NO 24
<211> LENGTH: 21
<212> TYPE: DNA
<213> ORGANISM: Artificial sequence
<220> FEATURE:
```

```
<223> OTHER INFORMATION: Synthetic Construct - amplification primer

<400> SEQUENCE: 24
atgacccgca gcttctaaca g                                              21

<210> SEQ ID NO 25
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 25
ctccgctcac agagctccta                                                20

<210> SEQ ID NO 26
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 26
ccaacatcac taacacaacc t                                              21

<210> SEQ ID NO 27
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 27
gggagttagt aaggggtttg                                                20

<210> SEQ ID NO 28
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 28
caacctatta aacaaaacta aatt                                           24

<210> SEQ ID NO 29
<211> LENGTH: 27
<212> TYPE: DNA
<213> ORGANISM: Artificial sequence
<220> FEATURE:
<223> OTHER INFORMATION: Synthetic Construct - amplification primer

<400> SEQUENCE: 29
agatttaata gagtgaaaat agagttt                                        27

<210> SEQ ID NO 30
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 30
ttattagttt aggggatagt tg                                             22
```

```
<210> SEQ ID NO 31
<211> LENGTH: 23
<212> TYPE: DNA
<213> ORGANISM: Artificial sequence
<220> FEATURE:
<223> OTHER INFORMATION: Synthetic Construct - amplification primer

<400> SEQUENCE: 31
acacaataaa caacctacta aat                                              23

<210> SEQ ID NO 32
<211> LENGTH: 19
<212> TYPE: DNA
<213> ORGANISM: Artificial sequence
<220> FEATURE:
<223> OTHER INFORMATION: Synthetic Construct - amplification primer

<400> SEQUENCE: 32
gagggtaagt ggtgataaa                                                   19

<210> SEQ ID NO 33
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 33
aacctactaa atccaaaaaa a                                                21

<210> SEQ ID NO 34
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 34
taggatttta ggtttattgt ta                                               22

<210> SEQ ID NO 35
<211> LENGTH: 19
<212> TYPE: DNA
<213> ORGANISM: Artificial sequence
<220> FEATURE:
<223> OTHER INFORMATION: Synthetic Construct - amplification primer

<400> SEQUENCE: 35
aaaaataaaa tattaaacc                                                   19

<210> SEQ ID NO 36
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 36
atatgtggga gtgagagata                                                  20

<210> SEQ ID NO 37
<211> LENGTH: 22
<212> TYPE: DNA
<213> ORGANISM: Artificial sequence
<220> FEATURE:
<223> OTHER INFORMATION: Synthetic Construct - amplification primer
```

<400> SEQUENCE: 37
caacaacaaa caataataat aa                                    22

<210> SEQ ID NO 38
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 38
ttgagttttt ttattgatag tg                                    22

<210> SEQ ID NO 39
<211> LENGTH: 21
<212> TYPE: DNA
<213> ORGANISM: Artificial sequence
<220> FEATURE:
<223> OTHER INFORMATION: Synthetic Construct - amplification primer

<400> SEQUENCE: 39
tctaaatcct attttcctac t                                     21

<210> SEQ ID NO 40
<211> LENGTH: 24
<212> TYPE: DNA
<213> ORGANISM: Artificial sequence
<220> FEATURE:
<223> OTHER INFORMATION: Synthetic Construct - amplification primer

<400> SEQUENCE: 40 gttttttat tgatagtgag agat                                   24

<210> SEQ ID NO 41
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 41
taacaaacct ttaatccaat                                       20

<210> SEQ ID NO 42
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 42
tttagtgagg atgatgtaat at                                    22

<210> SEQ ID NO 43
<211> LENGTH: 22
<212> TYPE: DNA
<213> ORGANISM: Artificial sequence
<220> FEATURE:
<223> OTHER INFORMATION: Synthetic Construct - amplification primer

<400> SEQUENCE: 43
caacttaata aaaataaacc ca                                    22

<210> SEQ ID NO 44
<211> LENGTH: 24

```
<212> TYPE: DNA
<213> ORGANISM: Artificial sequence
<220> FEATURE:
<223> OTHER INFORMATION: Synthetic Construct - amplification primer

<400> SEQUENCE: 44
ataatgtttt agtaagtgtt ggat                                        24

<210> SEQ ID NO 45
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 45
acaattacaa acctttaacc                                             20

<210> SEQ ID NO 46
<211> LENGTH: 20
<212> TYPE: DNA
<213> ORGANISM: Artificial sequence
<220> FEATURE:
<223> OTHER INFORMATION: Synthetic Construct - amplification primer

<400> SEQUENCE: 46
aattcattca acatccattc                                             20

<210> SEQ ID NO 47
<211> LENGTH: 26
<212> TYPE: DNA
<213> ORGANISM: Artificial sequence
<220> FEATURE:
<223> OTHER INFORMATION: Synthetic Construct - amplification primer

<400> SEQUENCE: 47
ggtttaatat tatttattat tttgga                                      26

<210> SEQ ID NO 48
<211> LENGTH: 25
<212> TYPE: DNA
<213> ORGANISM: Artificial sequence
<220> FEATURE:
<223> OTHER INFORMATION: Synthetic Construct - amplification primer

<400> SEQUENCE: 48
ctcttacctt cctatactct ctaaa                                       25

<210> SEQ ID NO 49
<211> LENGTH: 28
<212> TYPE: DNA
<213> ORGANISM: Artificial sequence
<220> FEATURE:
<223> OTHER INFORMATION: Synthetic Construct - amplification primer

<400> SEQUENCE: 49
agagtgtagt tgtaagattt aatagagt                                    28
```

METHOD FOR THE IN VITRO DIAGNOSIS OR PROGNOSIS OF TESTICULAR CANCER

Testicular cancer represents 1 to 2% of cancers in men, and 3.5% of urological tumors. It is the most common tumor in young men, and rare before 15 years of age and after 50 years of age. The risk is highest in patients who are seropositive for HIV. Seminoma is the most common form of testicular cancer (40%), but many other types of cancer exist, among which are embryonic carcinoma (20%), teratocarcinoma (30%) and choriocarcinoma (1%).

The diagnosis of testicular cancer is first clinical: it often presents in the form of a hard and irregular swelling of the testicle. An ultrasound confirms the intratesticular tumor and Doppler ultrasound demonstrates the increase in vascularization in the tumor. In some cases, a magnetic resonance examination (testicular MRI) can be useful. A thoracic, abdominal and pelvic scan makes it possible to investigate whether there is any lymph node involvement of the cancer. A blood sample for assaying tumor markers is virtually systematic. It makes it possible to orient the diagnosis of the type of tumor. Two main tumor markers are used and assayed in the blood: β-HCG and α-foetoprotein. However, these markers are not very specific and, furthermore, if the concentration of these markers is at physiological levels, this does not mean that there is an absence of tumor. At the current time, the final diagnosis and final prognosis are given after ablation of the affected testicle (orchidectomy), which constitutes the first stage of treatment. Next, depending on the type of cancer and on its stage, a complementary treatment by radiotherapy or chemotherapy is applied. There is therefore a real need for having markers which are specific for testicular cancer and which, in addition, make it possible to establish as early a diagnosis and prognosis as possible.

The rare event represented by the infection of a germline cell by an exogenous provirus results in the integration, into the host's genome, of a proviral DNA or provirus, which becomes an integral part of the genetic inheritance of the host. This endogenous provirus (HERV) is therefore transmissible to the next generation in Mendelien fashion. It is estimated that there are approximately a hundred or so HERV families representing approximately 8% of the human genome. Each of the families has from several tens to thousands of loci, which are the result of intracellular retrotranspositions of transcriptionally active copies. The loci of the contemporary HERV families are all replication-defective, which signifies loss of the infectious properties and therefore implies an exclusively vertical (Mendelien) transmission mode.

HERV expression has been particularly studied in three specific contexts, placentation, autoimmunity and cancer, which are associated with cell differentiation or with the modulation of immunity. It has thus been shown that the envelope glycoprotein of the ERVWE1 locus of the HERV-W family is involved in the fusion process resulting in syncytiotrophoblast formation. It has, moreover, been suggested that the Rec protein, which is a splice variant of the env gene of HERV-K, could be involved in the testicular tumorogenesis process. However, the following question has not yet been answered: are HERVs players or markers in pathological contexts?

The present inventors have now discovered and demonstrated that nucleic acid sequences belonging to loci of the HERV-W family are associated with testicular cancer and that these sequences are molecular markers for the pathological condition. The sequences identified are U3 retroviral promoter sequences of 5' LTRs (Long Terminal Repeats) which are hypomethylated in a cancerous biological sample.

In mammals, DNA can be methylated on the cytosines preceding a guanine (CpG doublet). This involves the transfer of a methyl group from S-adenosyl methionine to a cytosine residue so as to form 5-methylcytosine. The methylation of CpG doublets located in a promoter sequence generally results in an underexpression, or even a lack of expression, of the associated gene. Conversely, if the CpG doublets contained in a promoter sequence are hypomethylated, the expression of the associated gene is favored. The role of methylation in carcinogenesis has been recently studied. Thus, hypermethylation on the CpG doublets can result in the underexpression of a tumor suppressor gene, whereas, conversely, hypomethylation of CpG doublets can cause the activation of protooncogenes.

The subject of the present invention is therefore a method for in vitro, diagnosis or prognosis of testicular cancer, in a biological sample from a patient suspected of suffering from testicular cancer, characterized in that it comprises a step of detecting the presence or absence of methylation of CpG dinucleotides in at least one genomic DNA target sequence of the sample, the target sequence being selected from at least one of the sequences identified in SEQ ID Nos. 1 to 7 or from at least one sequence which exhibits at least 99% identity, preferably at least 99.5% identity, and advantageously at least 99.6% identity, with one of the sequences identified in SEQ ID Nos. 1 to 7 and the sequences complementary thereto.

The percentage identity described above has been determined while taking into consideration the nucleotide diversity in the genome. It is known that nucleotide variability is higher in the regions of the genome that are rich in repeat sequences than in the regions which do not contain repeat sequences. By way of example, D. A. Nickerson et al.,[1] have shown a diversity of approximately 0.3% (0.32%) in regions containing repeat sequences.

The sequences SEQ ID Nos. 1 to 6 correspond, respectively, to the sequences of the U3 retroviral promoters of the HW4TT, HW2TT, HW13TT, HWXTT, HW21TT and ERVWE1 loci, and SEQ ID No. 7 corresponds to the sequence of the activator plus the sequence of the U3 region of ERVWE1.

The sample from the patient will generally comprise cells (such as the testicular cells). They may be present in a tissue sample (such as the testicular tissue) or be found in the circulation. In general, the sample is a testicular tissue extract or a biological fluid, such as blood, serum, plasma, urine or else seminal fluid.

More particularly, the method comprises:
(i) extraction of the genomic DNA to be analyzed from the sample,
(ii) treatment of the extracted genomic DNA with one or more reagents so as to convert the cytosine bases, of the CpG dinucleotides, which are nonmethylated at position 5, into uracil,
(iii) at least one amplification of the treated DNA by bringing into contact with at least two primers,
(iv) determination, on the basis of the presence or absence of methylation of the cytosines of the CpG dinucleotides, of a methylation state of said target sequence or of a value which reflects the methylation state of the target sequence, for example the ratio of the number of methylated cytosines of the CpG dinucleotides/total number of cytosines of the CpG dinucleotides. In particular, if the ratio, corresponding to a percentage methylation, is less than or equal to 80%, preferably less than or equal to 60%, and advantageously less than or equal to 30%, this can be correlated with a presumption of testicular cancer.

If necessary, the method comprises a second amplification step after the amplification step described in (iii), which consists in bringing the amplicons obtained in (iii) into contact with at least two primers in order to amplify the target sequence.

The term "target sequence" is intended to mean a sequence or the sequences of a set of clones.

The determination, in the DNA, of the degree of methylation is carried out by any suitable technique. The methylation state or status of a DNA sequence can be established by methods using methylation-sensitive restriction enzymes or by methods involving a chemical modification of the DNA with sodium bisulfite, hydrogen sulfite or disulfite, preferably with a solution of sodium bisulfite, which converts the non-methylated cytosines into uracils while at the same time not modifying the 5-methylcytosines. The analysis of the methylation can be carried out by conventional methods, such as sequencing, hybridization or PCR. Several methods of analysis use the ammonium bisulfite conversion technique, such as bisulfite sequencing PCR (conversion with ammonium bisulfite, amplification of the sequence of interest and sequencing), MSP (Methylation Specific PCR) and MSO (Methylation Specific Oligonucleotide Microarray) using DNA chips specific for the modified DNA. All these methods are well known to those skilled in the art and mention may be made, by way of illustration, of S. E. Cottrell[2].

Thus, in step (ii) of the abovementioned method, the treatment of the genomic DNA comprises the use of a solution selected from the group consisting of hydrogen sulfite, disulfite and bisulfite, and combinations thereof; preferably, a solution of sodium bisulfite.

In one embodiment of the invention, the method for in vitro diagnosis and/or prognosis of testicular cancer comprises:
(i) extraction of the DNA to be analyzed from the sample from the patient,
(ii) determination, in the DNA to be analyzed, of the degree (percentage) of methylation of the cytosines of the CpG dinucleotides included in at least one of the DNA sequences identified in SEQ ID Nos. 1 to 7 or in at least one sequence which exhibits at least 99% identity, preferably at least 99.5%, advantageously at least 99.6% identity, with a sequence identified in SEQ ID Nos. 1 to 7, and
(iii) comparison of the degree (percentage) of methylation of the cytosines in one or more DNA sequences as defined in (ii) with the degree (percentage) of methylation of said cytosines of said sequence(s) present in the DNA extracted from a noncancerous biological sample; if the degree of methylation in the DNA to be analyzed is determined as being less than the degree of methylation in the DNA extracted from the noncancerous biological sample, this can be correlated with the diagnosis or prognosis of a testicular cancer.

The term "hypomethylated sequence" is therefore intended to mean a DNA sequence comprising one or more CpG doublets, in which a cytosine of at least one CpG dinucleotide or doublet is not methylated at position 5 (i.e. which does not contain a $CH_3$ radical at the fifth position of the cytosine base) in comparison with the same DNA sequence derived from the same type of noncancerous sample. In order to determine the methylation state or status of a target sequence, the following ratio can be calculated:
number of methylated cytosines of the CpG dinucleotides/ total number of cytosines of the CpG dinucleotides. If the ratio, corresponding to a percentage methylation, is less than or equal to 80%, preferably less than or equal to 60%, and advantageously less than or equal to 30%, this can be correlated with a presumption of testicular cancer.

The subject of the invention is also an isolated nucleic acid sequence consisting of at least one DNA sequence selected from the sequences identified in SEQ ID Nos. 1 to 7 or from at least one sequence which exhibits at least 99% identity (preferably at least 95.5% or 95.6% identity) with one of the sequences identified in SEQ ID Nos. 1 to 7 and the sequences complementary thereto. The abovementioned sequences which are associated with testicular cancer are used as molecular markers for testicular cancer.

FIGURES

Figure 4:
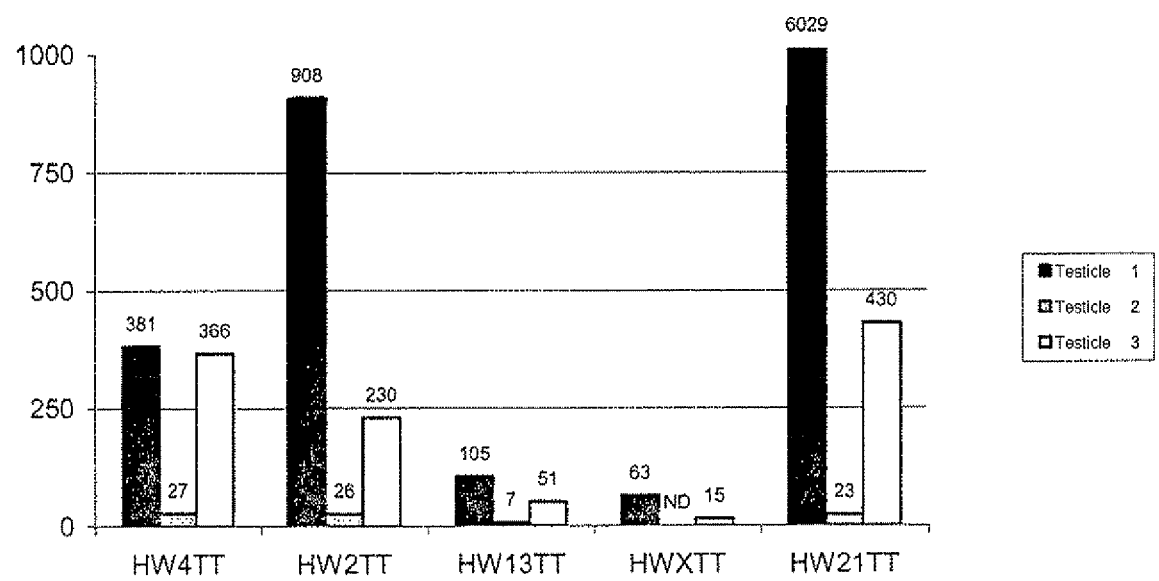
Figure 5:
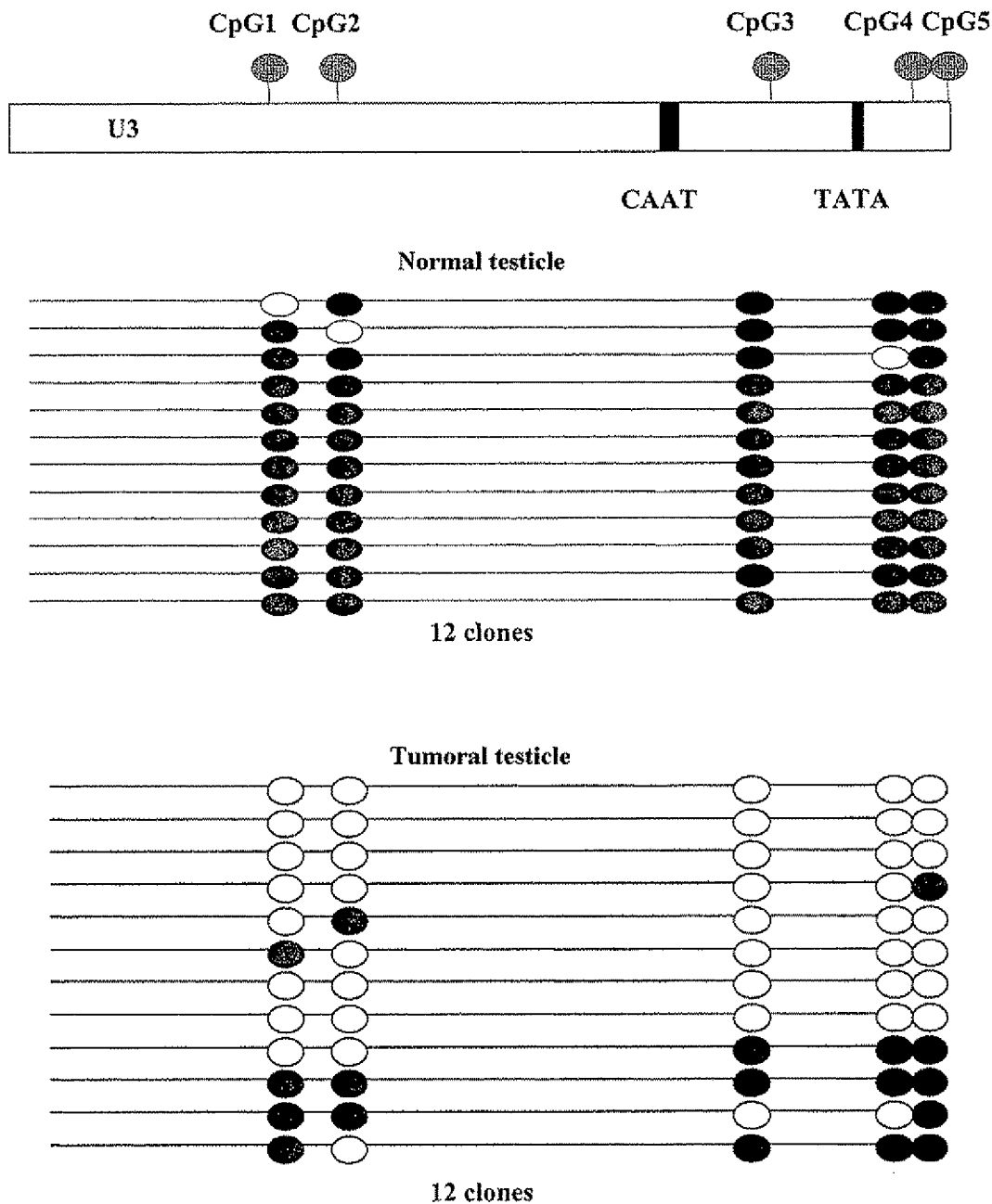
Figure 6:
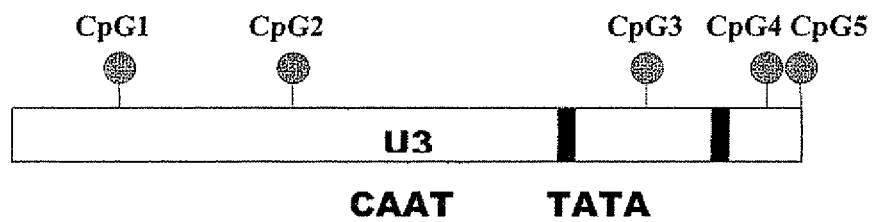
Figure 6:
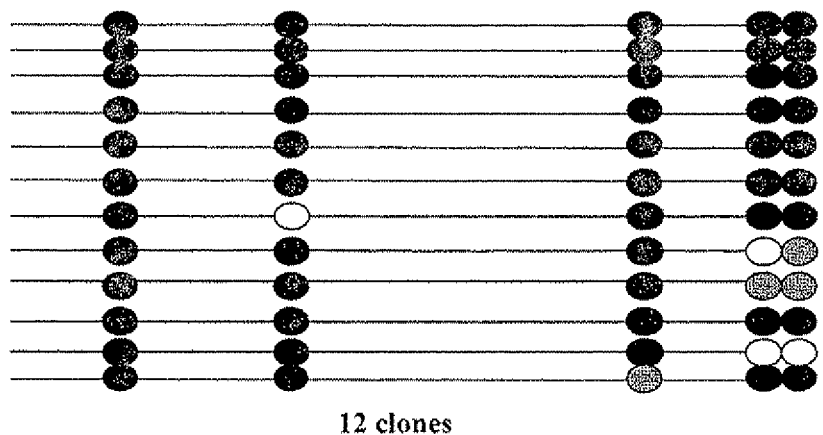
Figure 6:
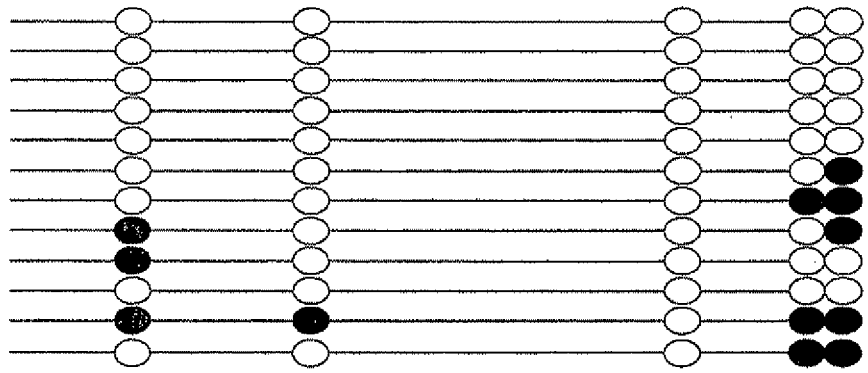
Figure 7:
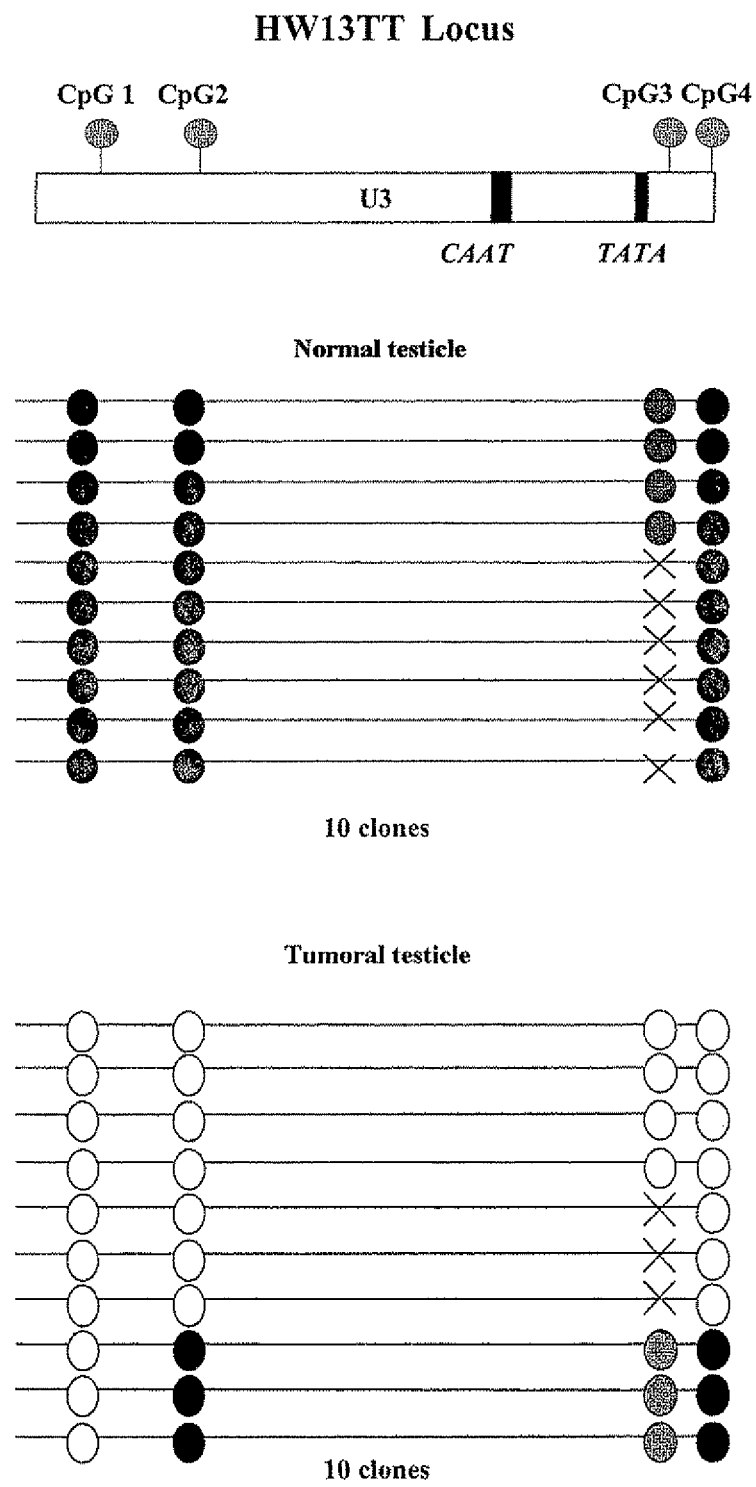
Figure 8:
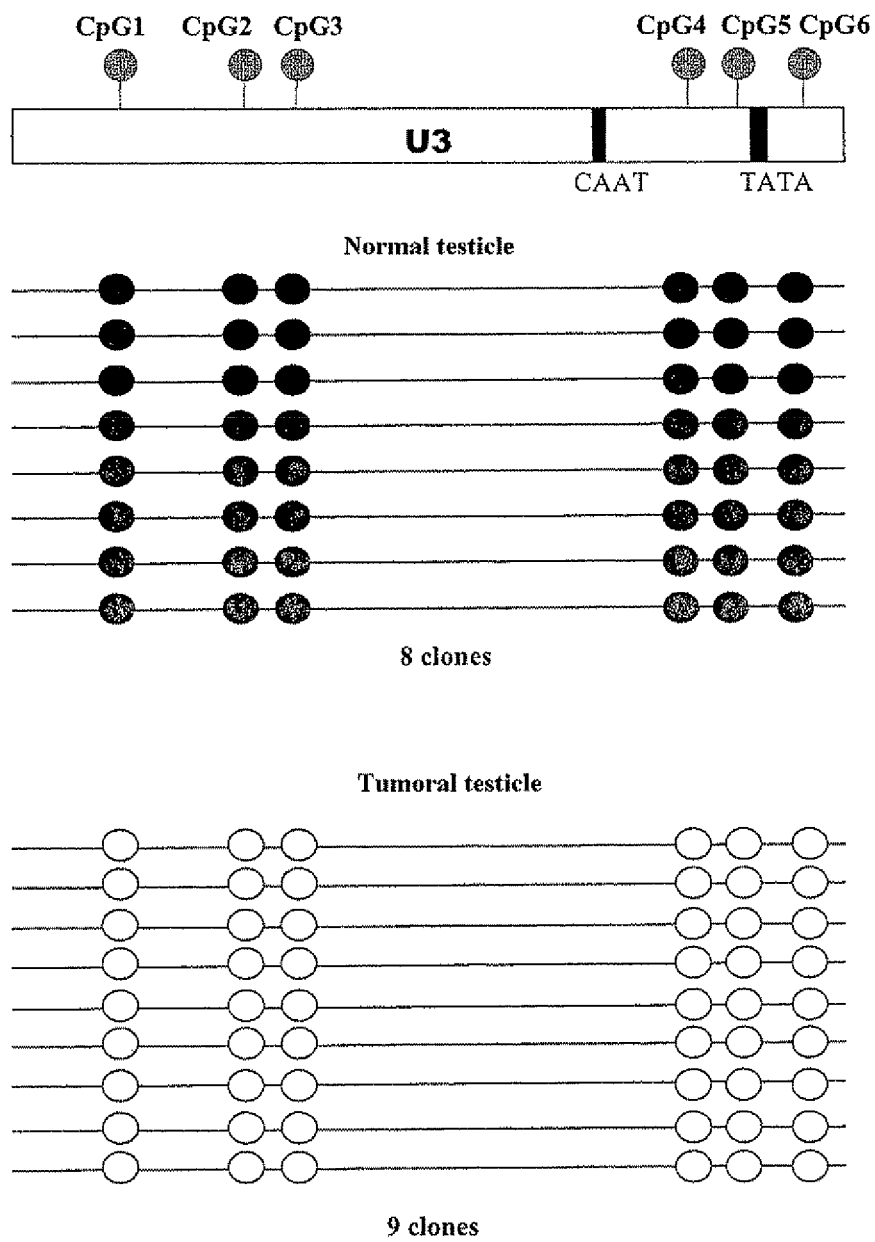
Figure 9:
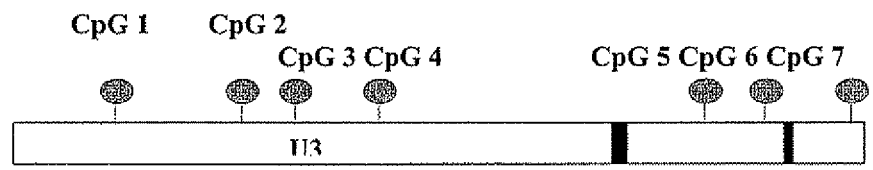
Figure 9:
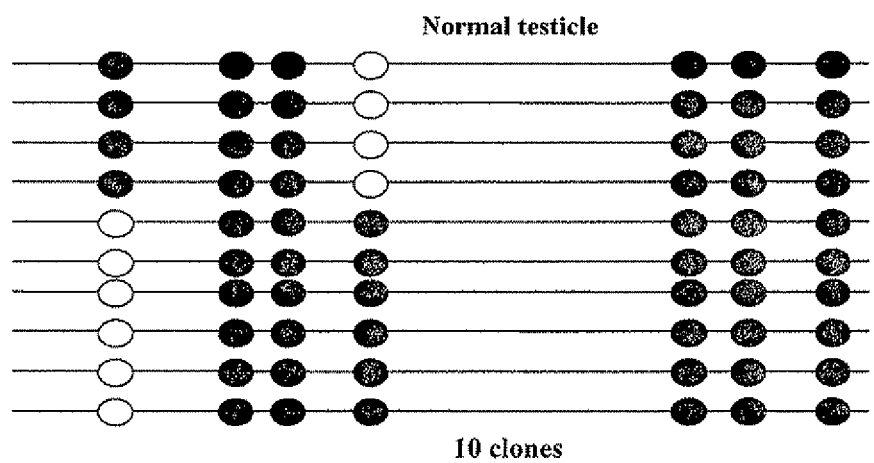
Figure 9:
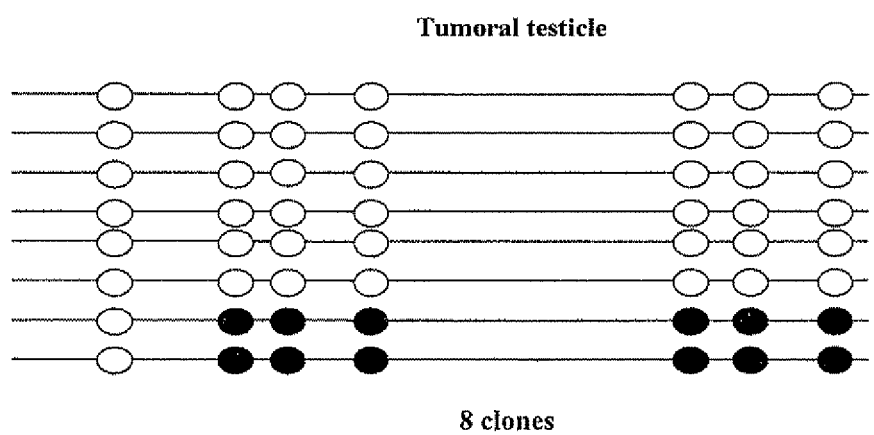
Figure 10:
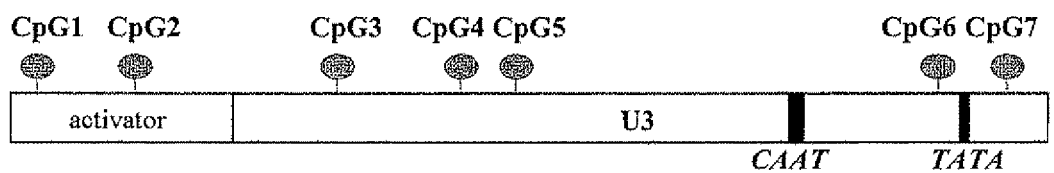
Figure 10:
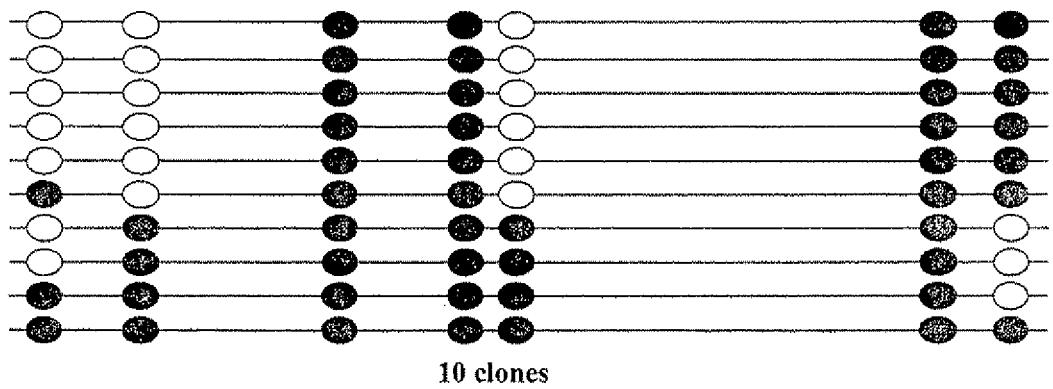
Figure 10:
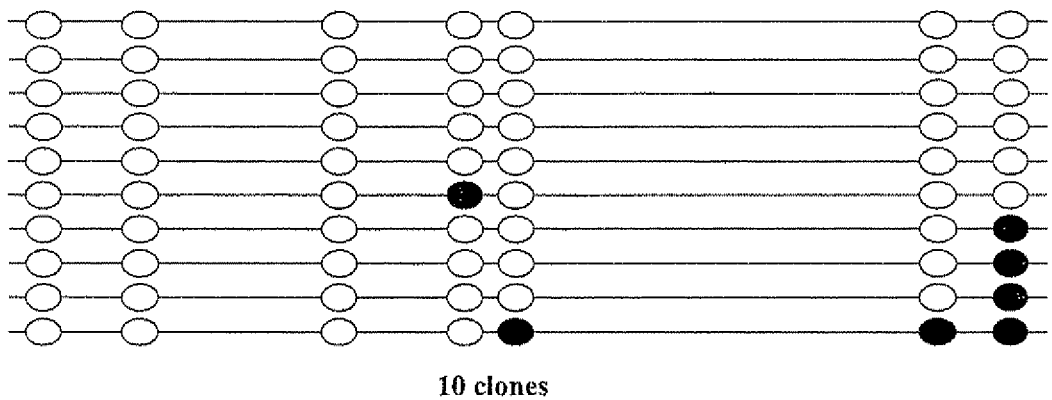

FIG. 4 is a histogram representing the increase in expression of five loci (HW4TT, HW2TT, HW13TT, HWXTT and HW21TT), respectively, in three pairs of testicular samples (testicle 1, testicle 2 and testicle 3), based on a comparative tumor sample/healthy sample quantification. The loci are represented along the x-axis and the factors of increase of expression between tumor tissue and healthy tissue are represented along the y-axis.

FIGS. 5 to 10 represent the methylation status of the U3 region of unique LTR or of the 5' LTR of the various loci, respectively HW4TT, HW2TT, HW13TT, HWXTT, HW21TT and ERVWE1 in the healthy testicle (normal) and in the tumoral testicle derived from the same patient, after amplification and analysis of the sequences obtained.

EXAMPLES

Example 1

Identification of HERV-W Loci Expressed in Cancerous Tissues

Method:

The identification of expressed HERV-W loci is based on the design of a high-density DNA chip in the GeneChip format proposed by the company Affymetrix. It is a specially developed, custom-made chip, the probes of which correspond to HERV-W loci. The sequences of the HERV-W family were identified from the GenBank nucleic databank using the Blast algorithm (Altschul et al., 1990) with the sequence of the ERVWE1 locus, located on chromosome 7 at 7q21.2 and encoding the protein called syncytin. The sequences homologous to HERV-W were compared to a library containing reference sequences of the HERV-W family (ERVWE1) cut up into functional regions (LTR, gag, pal and env), using the RepeatMasker software (A. F. A. Smit and P. Green). These elements constitute the HERVgDB bank.

The probes making up the high-density chip were defined on a criterion of uniqueness of their sequences in the HERVgDB bank. The HERV-W proviral and solitary LTRs contained in the HERVgDB bank were extracted. Each of these sequences was broken down into a set of sequences of 25 nucleotides (25-mers) constituting it, i.e. as many potential probes. The evaluation of the uniqueness of each probe was carried out by means of a similarity search with all the 25-mers generated for all the LTRs of the family under consideration. This made it possible to identify all the 25-mers of unique occurrence for each family of HERV. Next, some of these 25-mers were retained as probes. For each U3 or U5 target region, a set of probes was formed on the basis of the probes identified as unique.

Figure 1:
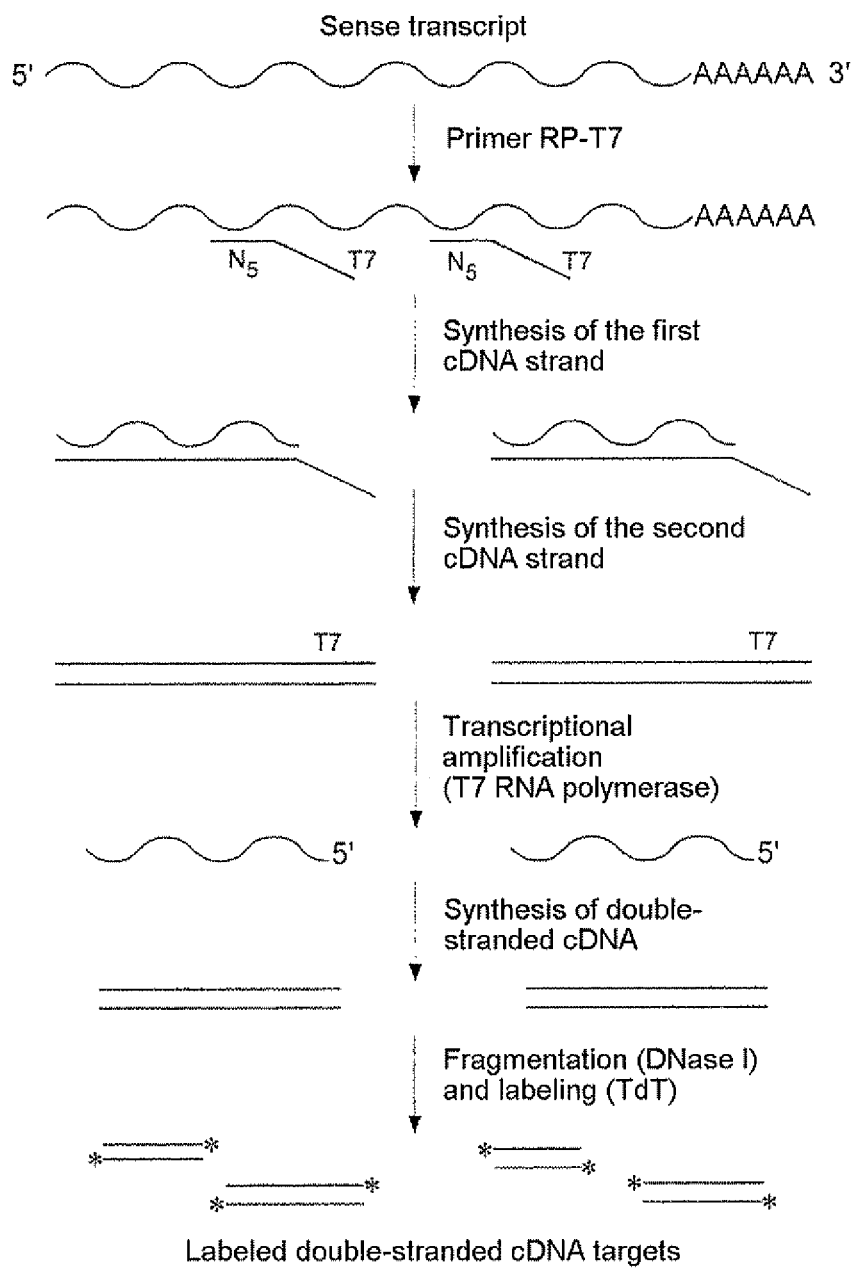
FIG. 1 represents the principle of the WTA method for amplifying RNAs.

The samples analyzed using the HERV high-density chip correspond to RNAs extracted from tumors and to RNAs extracted from the healthy tissues adjacent to these tumors. The tissues analyzed are: uterus, colon, lung, breast, testicle, prostate and ovary. Placental RNAs (health tissue only) were also analyzed. For each sample, 400 ng of total RNA were amplified by means of an unbiased transcriptional method known as WTA. The principle of WTA amplification is the following: primers (RP-T7) comprising a random sequence and a T7 promoter sequence are hybridized to the transcripts; double-standard cDNAs are synthesized and serve as a template for transcriptional amplification by the T7 RNA polymerase; the antisense RNAs generated are converted to double-stranded cDNAs which are then fragmented and labeled by introducing biotinylated nucleotide analogs at the 3'OH ends using terminal transferase (TdT) (cf. FIG. 1).

Figure 2:
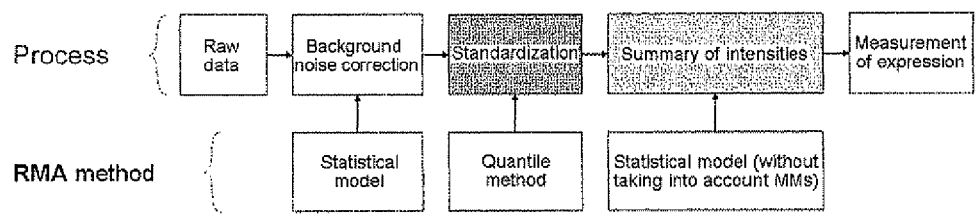
FIG. 2 represents a synoptic scheme of the nature and the sequence of the various steps for preprocessing DNA-chip data according to the RMA method.

For each sample, 16 µg of biotin-labeled amplification products were hybridized to a DNA chip according to the protocol recommended by the company Affymetrix. The chips were then washed and labeled, according to the recommended protocol. Finally, the chips were read by a scanner in order to acquire the image of their fluorescence. The image analysis carried out using the GCOS software makes it possible to obtain numerical values of fluorescence intensity which are preprocessed according to the RMA method (cf.: FIG. 2) before being able to carry out a statistical analysis in order to identify the HERV loci specifically expressed in certain samples.

Comparison of the means of more than two classes of samples was carried out by the SAM procedure applied to a Fisher test.

Figure 3:
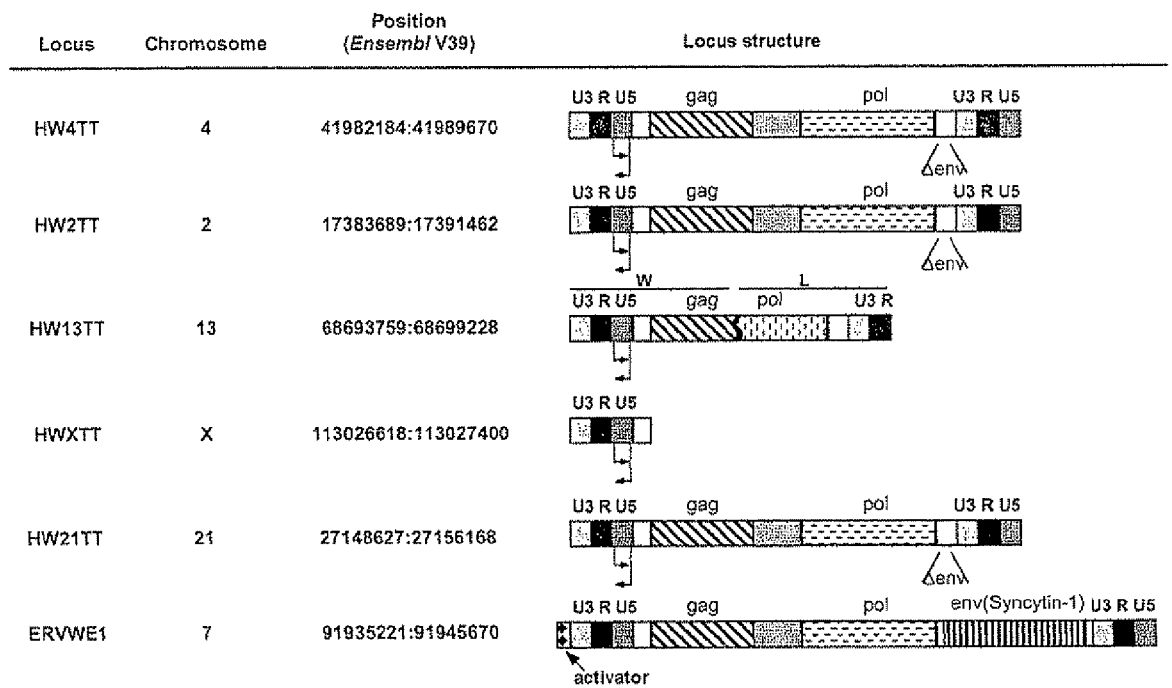
FIG. 3 illustrates the nomenclature, the position and the structure of the HERV-W loci overexpressed and exhibiting a loss of methylation in the tumoral testicle.

Results:

The processing of the data generated by the analysis on DNA chip using this method made it possible to identify six sets of probes corresponding to an overexpression in just one sample: the tumoral testicle. These five sets of probes are specific for six precise loci referenced HW4TT, HW2TT, HW13TT, HWXTT, HW21TT and ERVWE1 (cf.: FIG. 3). The information relating to the abovementioned loci are summarized in Table 1 below.

TABLE 1

| Locus | SEQ ID No: | Chromosome | Position* |
|---|---|---|---|
| HW4TT | 8 | 4 | 43982184:41989670 |
| HW2TT | 9 | 2 | 17383689:17391462 |

TABLE 1-continued

| Locus | SEQ ID No: | Chromosome | Position* |
|---|---|---|---|
| HW13TT | 10 | 13 | 68693759:68699228 |
| HWXTT | 11 | X | 113026618:113027400 |
| HW21TT | 12 | 21 | 27148627:27156168 |
| ERVWE1 | 13 | 7 | 91935221:91945670 |

*Position given in relation to ensemble version No. 39 (June 2006) (NCBI No. 36) http://www.ensembl.org/Homo_sapiens/index.html The HW13TT locus is a chimeric provirus of HERV-W/L type resulting from the recombination of an HERV-W provirus and an HERV-L provirus. This chimera is such that the 5' region made up of the sequence starting from the beginning of the 5' LTR to the end of the determined gag fragment is of W type and the 3' region made up of the sequence starting from the subsequent pol fragment to the end of the 3' LTR (U3-R only) is of L type. This results in a fusion of the 3' gag W-5' pol L regions.

Example 2

Validation of the Loci Overexpressed in the Tumoral Testicle and Determination of the Associated Induction Factor Principle:

The six loci identified as overexpressed in the tumoral testicle by means of the high-density HERV chip were validated by real-time RT-PCR on three pairs of testicular samples. The specificity of this overexpression is evaluated by analyzing samples originating from other tissues. To this end, specific amplification systems were developed and used for the loci identified, as described in Table 2 below.

TABLE 2

| Locus | Sense primer (SEQ ID No:) | Antisense primer (SEQ ID No:) |
|---|---|---|
| G6PD gene | TGCAGATGCTGTGTCTGG (14) | CGTACTGGCCCAGGACC (15) |
| HW4TT | GGTTCGTGCTAATTGAGCTG (16) | ATGGTGGCAAGCTTCTTGTT (17) |
| HW2TT | TGAGCTTTCCCTCACTGTCC (18) | TGTTCGGCTTGATTAGGATG (19) |
| HW13TT | CATGGCCCAATATTCCATTC (20) | GGTCCTTGTTCACAGAACTCC (21) |
| HWXTT | CCGCTCCTGATTGGACTAAA (22) | CGTGGGTCAAGGAAGAGAAC (23) |
| HW21TT | ATGACCCGCAGCTTCTAACAG (24) | CTCCGCTCACAGAGCTCCTA (25) |

The expression of these loci is standardized with respect to that of a suitable housekeeping gene: G6PD. This quantification of expression was carried out using an Mx3005P real-time RT-PCR machine, marketed by the company Stratagene.

Results:

The study of the three pairs of testicular samples indicates that all the putative loci identified, with the exception of HWXTT, the expression of which could not be quantified in the second testicular RNA pair, are overexpressed in the tumoral testicle compared with the health tissue (cf.: FIG. 4).

The analysis of pairs of samples originating from other tissues (colon, uterus, breast, ovary, lung and prostate) shows that the overexpression phenomenon is restricted to the tumoral testicle. Consequently, the expression of the five identified loci assumes the nature of a marker specific for testicular cancer.

Example 3

Epigenetic Control of Transcription

Principle:

DNA methylation is an epigenetic modification which takes place, in eukaryotics, by the addition of a methyl group to the cytosines of 5'-CpG dinucleotides, and results in transcriptional repression when this modification occurs within the nucleotide sequence of a promoter. Apart from a few exceptions, human endogenous sequences of retroviral origin are restricted, owing to this methylation process, to a silent transcriptional state in the cells of the organism under physiological conditions.

In order to analyze the methylation status of the unique LTR or of the 5' LTR of the five loci, the "bisulfite sequencing PCR" method was used. This method makes it possible, on the basis of sequencing a representative sample of the population, to identify the methylation state of each CG dinucleotide on each of the sequences within the tissue studied.

Since the methylation information is lost during the amplification steps, it is advisable to translate the methylation information actually within the nucleotide sequence by means of the method of treating the genomic DNA with sodium bisulfite. The action of the bisulfite (sulfonation), followed by hydrolytic deamination and then alkaline desulfonation, in fact makes it possible to modify all the cytosines contained in the genomic DNA, into uracil. The speed of deamination of sulfonated cytosines (C) is, however, much higher than that of the sulfonated 5-methyl-Cs. It is therefore possible, by limiting the reaction time to 16 hours, to convert strictly the non-methylated cytosines to uracil (U), while at the same time preserving the cytosines which have a methyl group. After the sodium bisulfite treatment, the sequence of interest is amplified from the genomic DNA derived from the tumoral testicular section and from that derived from the adjacent healthy testicular section, by polymerase chain reaction (PCR) in two stages. The first PCR enables a specific selection of the sequence of interest, the second, "nested", PCR makes it possible to amplify this sequence.

Since the DNA sequence had been modified by the bisulfite, the design of the primers took into account the code change (C to U), and the primers were selected so as to hybridize to a region containing no CpG (their methylation state, and therefore their conversion state, being a priori unknown).

The sequences of the primers used are described in Tables 3 to 8 below.

TABLE 3

HW4TT locus

| Amplification | Sense primer 5'→3' (SEQ ID No.:) | Antisense primer 5'→3' (SEQ ID No.:) |
|---|---|---|
| First PCR | CCAACATCACTAACACAACCT (26) | GGGAGTTAGTAAGGGGTTTG (27) |
| Nested PCR | CAACCTATTAAACAAAACTAAATT (28) | AGATTTAATAGAGTGAAAATAGAGTTT (29) |

TABLE 4

HW2TT locus

| Amplification | Sense primer 5'→3' (SEQ ID No.:) | Antisense primer 5'→3' (SEQ ID No.:) |
|---|---|---|
| First PCR | TTATTAGTTTAGGGGATAGTTG (30) | ACACAATAAACAACCTACTAAAT (31) |
| Nested PCR | GAGGGTAAGTGGTGATAAA (32) | AACCTACTAAATCCAAAAAAA (33) |

TABLE 5

HW13TT locus

| Amplification | Sense primer 5'→3' (SEQ ID No.:) | Antisense primer 5'→3' (SEQ ID No.:) |
|---|---|---|
| First PCR | TAGGATTTTAGGTTTATTGTTA (34) | AAAAATAAAATATTAAACC (35) |
| Nested PCR | ATATGTGGGAGTGAGAGATA (36) | CAACAACAAACAATAATAATAA (37) |

TABLE 6

HWXTT locus

| Amplification | Sense primer 5'→3' (SEQ ID No.:) | Antisense primer 5'→3' (SEQ ID No.:) |
|---|---|---|
| First PCR | TTGAGTTTTTTTATTGATAGTG (38) | TCTAAATCCTATTTTCCTACT (39) |
| Nested PCR | GTTTTTTTATTGATAGTGAGAGAT (40) | TAACAAACCTTTAATCCAAT (41) |

TABLE 7

HW21TT locus

| Amplification | Sense primer 5'→3' (SEQ ID No.:) | Antisense primer 5'→3' (SEQ ID No.:) |
|---|---|---|
| First PCR | TTTAGTGAGGATGATGTAATAT (42) | CAACTTAATAAAAATAAACCCA (43) |
| Nested PCR | ATAATGTTTTAGTAAGTGTTGGAT (44) | ACAATTACAAACCTTTAACC (45) |

TABLE 8

ERVWE1 locus

| Amplification | Sense primer 5'→3' (SEQ ID No.:) | Antisense primer 5'→3' (SEQ ID No.:) |
|---|---|---|
| First PCR | AATTCATTCAACATCCATTC (46) | GGTTTAATATTATTTATTATTTTGGA (47) |
| Nested PCR | CTCTTACCTTCCTATACTCTAAA (48) | AGAGTGTAGTTGTAAGATTTAATAGAGT (49) |

After extraction on a gel and purification, the amplicons are cloned into plasmids, and the latter are used to transform competent bacteria. About twelve plasmid DNA mini preparations are carried out using the transformed bacteria and the amplicons contained in the plasmids are sequenced. The sequences obtained are then analyzed (cf.: FIGS. 5 to 10).

Results:

The analysis of the 5' region of the transcripts of the loci identified was carried out by means of the 5' Race technique. It in particular made it possible to show that the transcription is started at the beginning of the R region of the proviral 5' LTR. This reflects the existence of a promoter role for the U3 region of the proviral 5' LTR.

1. Methylation State of the U3 Sequences of the 5' LTR of the HW4TT Locus:

The U3 sequence of the 5' LTR of the HW4TT locus of reference contains 5 CpG sites:

a) in the sample of healthy testicular tissue: out of 12 sequences analyzed, 9 are completely methylated. The other 3 each time exhibit 1 CpG nonmethylated out of the 5 contained in the U3 region. This therefore represents an overall methylation of the U3 region of the 5' LTR of the HW4TT locus amounting to 95% in the healthy testicular sample;

b) in the sample of tumoral testicular tissue: out of 12 sequences analyzed, 5 (i.e. 41.66% of the sequences) are completely demethylated, 3 sequences have 4 CpGs out of 5 nonmethylated, 2 sequences have 2 CpGs out of 5 nonmethylated, 1 sequence has 1 CpG out of 5 nonmethylated, and 1 sequence remains completely methylated. This therefore represents an overall methylation of the U3 region of the 5' LTR of the HW4TT locus amounting to 30% in the tumoral testicular sample.

2. Methylation State of the U3 Sequences of the 5' LTR of the HW2TT Locus:

The U3 sequence of the 5' LTR of the HW2TT locus of reference contains 5 CpG sites:

a) in the sample of healthy testicular tissue: out of 12 sequences analyzed, 9 are completely methylated, 1 has its $2^{nd}$ CpG nonmethylated, 1 has the CpG at position 4 nonmethylated, 1 has the CpGs at positions 4 and 5 nonmethylated, and 3 sequences have point mutations on one or two CpGs (one in position 3, one in position 5 and one in positions 4 and 5), very probably reflecting PCR artifacts. This therefore represents an overall methylation of the U3 region of the 5' LTR of the HW2TT locus amounting to 92.9% in the healthy testicular sample;

b) in the sample of tumoral testicular tissue: out of 12 sequences analyzed, 6 are completely demethylated, 5 sequences have one or two methylated CpG(s) (1 at position 1, 1 other at position 5, 1 on positions 1 and 5, 2 at positions 4 and 5 and 1 at position 3). Finally, one sequence has 4 CpGs methylated out of 5 (positions 1, 2, 4 and 5). This corresponds to an overall methylation of the U3 region of the 5' LTR of the HW2TT locus amounting to 20% in the tumoral testicular sample.

3. Methylation State of the U3 Sequences of the 5' LTR of the HW13TT Locus:

The U3 sequence of the 5' LTR of the HW13TT locus of reference contains 3 CpG sites:

a) in the sample of healthy testicular tissue: an additional CpG, compared with the reference sequence, is found in 4 of the 10 clones studied for this locus. It is located between CpGs 2 and 3 and is methylated. In the other 6 clones, this site is mutated compared with the reference sequence. The other 3 CpGs of the U3 region are methylated in the 10 sequences analyzed. This therefore represents an overall methylation of the U3 region of the 5' LTR of the HW13TT locus amounting to 100% in the healthy testicular sample;

b) in the sample of tumoral testicular tissue: the additional CpG indicated above is also found. It is demethylated in 4 of the 10 sequences analyzed, mutated in 3 other sequences, and its methylation state is indeterminate in the last 3 sequences. 7 sequences out of 10 are completely demethylated and the other 3 are methylated on the $2^{nd}$ and on the $3^{rd}$ CpG. This corresponds to an overall methylation of the U3 region of the 5' LTR of the HW13TT locus amounting to 20% in the tumoral testicular sample.

4. Methylation State of the U3 Sequences of the Solitary LTR of the HWXTT Locus:

The U3 sequence of the 5' LTR of the HWXTT locus of reference contains 6 CpG sites:

a) in the sample of healthy testicular tissue: the 8 sequences analyzed are completely methylated, which corresponds to a methylation percentage of 100% in the healthy testicular sample;

b) in the sample of tumoral testicular tissue: the 9 sequences analyzed 6 are completely demethylated, which corresponds to a methylation percentage of 0%.

5. Methylation State of the U3 Sequences of the 5' LTR of the HW21TT Locus:

The U3 sequence of the 5' LTR of the HW21TT locus of reference contains 7 CpG sites:

a) in the sample of healthy testicular tissue: the 10 sequences analyzed all have 6 CpGs methylated out of 7; for 6 of the sequences, the $1^{st}$ CpG is nonmethylated and for the other 4 sequences, the $4^{th}$ CpG is nonmethylated. This therefore represents an overall methylation of the U3 region of the 5' LTR of the HW21TT locus amounting to 85.7% in the healthy testicular sample;

b) in the sample of tumoral testicular tissue: out of 8 sequences analyzed, 6 are completely demethylated, 2 others exhibit a profile identical to one of those found in the healthy testicular tissue, namely 6 CpGs methylated and the $1^{st}$ CpG nonmethylated. This corresponds to an overall methylation of the U3 region of the 5' LTR of the HW21TT locus amounting to 21.4% in the tumoral testicular sample.

6. Methylation State of the Sequences of the Activator of the U3 of the 5' LTR of the ERVWE1 Locus:

The ERVWE1 locus comprises, in addition to its U3 promoter region, a known activator located directly upstream of the 5' LTR, and which contains two CpG sites (CpG 1 and 2). The U3 sequence of the 5' LTR of the ERVWE1 locus of reference contains, for its part, 5 CpG sites (CpGs 3 to 7):

a) in the sample of healthy testicular tissue: out of 10 sequences analyzed, 5 sequences have CpGs 1 and 2 (activator) and 5 (U3) nonmethylated, 1 sequence has CpGs 2 and 5 nonmethylated, 2 sequences have CpGs 1 (activator) and 7 (U3) nonmethylated, 1 sequence has CpG 7 only nonmethylated and, finally, 1 is completely methylated for the 7 CpGs. In total, this corresponds to a methylation percentage of 68.57% in the healthy testicular sample;

b) in the sample of tumoral testicular tissue: out of the 10 sequences analyzed, only 3 sequences exhibit, for each one, a unique methylated CpG (CpG 4 or CpG5 or CpG6), the other 7 sequences are completely demethylated, which corresponds to a methylation percentage of 4.29%.

The very high level of methylation of the U3 retroviral promoters of the loci considered, in the healthy tissue, indicates a repression of the transcriptional expression by an epigenetic mechanism. On the other hand, the low level of methylation of these same promoters in the tumoral tissue reflects a lifting of transcriptional inhibition, the result of which is the significantly higher expression demonstrated by means of the high-density HERV DNA chip and by means of the real-time RT-PCR. Thus, the U3 retroviral promoters of the loci considered appear to be specific markers for the tumoral nature of the testicle.

LITERATURE REFERENCES

[1] Nickerson D. A. et al., DNA sequence diversity in a 9.7-kb region of the human lipoprotein lipase gene, Nature Genetics, Vol. 19, pp 233-240 (1998).

[2] Cottrell S. E., Molecular diagnostic applications of DNA methylation technology, Clinical Biochemistry 37, pp 595-604 (2004).

The invention claimed is:

1. A method for in vitro diagnosis of testicular cancer, comprising:
obtaining a biological sample from a patient suspected of having testicular cancer;
performing an assay to determine the methylation status of CpG dinucleotides in a genomic DNA target sequence, the DNA target sequence being at least one sequence selected from the group consisting of sequences having at least 99% sequence identity with the full-length sequences of SEQ ID NOS: 1-5 and the sequences fully complementary thereto; and
diagnosing the patient with testicular cancer when the DNA target sequence is hypomethylated as compared to a methylation status indicative of the absence of testicular cancer, wherein the assay comprises:
extracting genomic DNA from the biological sample;
treating the extracted genomic DNA to convert cytosine bases of CpG dinucleotides that are nonmethylated at position 5 into uracil bases;
amplifying the treated genomic DNA target sequence; and
determining the methylation status of the CpG dinucleotides in the genomic DNA target sequence from the amplified genomic DNA target sequence.

2. The method of claim 1, wherein the extracted genomic DNA is treated using hydrogen sulfite, disulfite, bisulfite, or a combination thereof.

3. The method of claim 1, wherein the treated genomic DNA target sequence is amplified using at least one primer comprising a sequence selected from the group consisting of the full-length sequences of SEQ ID NOS: 26-45.

4. The method of claim 1, wherein the biological sample is a testicular tissue extract or a biological fluid.

5. The method of claim 1, wherein the biological sample is blood, serum, plasma, urine, or seminal fluid.

6. The method of claim 1, wherein the DNA target sequence is hypomethylated if 60% or less of the CpG dinucleotides are methylated.

7. The method of claim 1, wherein the DNA target sequence is hypomethylated if 30% or less of the CpG dinucleotides are methylated.

8. A method for in vitro diagnosis of testicular cancer, comprising: obtaining a biological sample from a patient suspected of having testicular cancer; performing an assay to determine the methylation status of CpG dinucleotides in a genomic DNA target sequence, the DNA target sequence being at least one sequence selected from the group consisting of the 5' LTR U3 promoter sequences of the HW4TT, HW2TT, HW 13TT, HWXTT, and HW21TT loci; and diagnosing the patient with testicular cancer when the DNA target sequence is hypomethylated as compared to a methylation status indicative of the absence of testicular cancer, wherein the assay comprises: extracting genomic DNA from the biological sample; treating the extracted genomic DNA to convert cytosine bases of CpG dinucleotides that are nonmethylated at position 5 into uracil bases; amplifying the treated genomic DNA target sequence; and determining the methylation status of the CpG dinucleotides in the genomic DNA target sequence from the amplified genomic DNA target sequence.

9. The method of claim 8, wherein the extracted genomic DNA is treated using hydrogen sulfite, disulfite, bisulfite, or a combination thereof.

10. The method of claim 8, wherein the treated genomic DNA target sequence is amplified using at least one primer comprising a sequence selected from the group consisting of the full-length sequences of SEQ ID NOS: 26-45.

11. The method of claim 8, wherein the biological sample is a testicular tissue extract or a biological fluid.

12. The method of claim 8, wherein the biological sample is blood, serum, plasma, urine, or seminal fluid.

13. The method of claim 8, wherein the DNA target sequence is hypomethylated if 60% or less of the CpG dinucleotides are methylated.

14. The method of claim 8, wherein the DNA target sequence is hypomethylated if 30% or less of the CpG dinucleotides are methylated.

* * * * *